(12) United States Patent
Neagle et al.

(10) Patent No.: US 7,552,642 B2
(45) Date of Patent: Jun. 30, 2009

(54) PRESSURE VESSEL TESTING

(75) Inventors: Paul W. Neagle, Westerville, OH (US); Laura J. Silva, Dublin, OH (US); Eric A. Daymo, Dublin, OH (US); David J Kuhlmann, Powell, OH (US); Marc Wagner, Saint-Maur-des-Fossés (CA)

(73) Assignee: Velocys, Inc., Plain City, OH (US)

( * ) Notice: Subject to any disclaimer, the term of this patent is extended or adjusted under 35 U.S.C. 154(b) by 0 days.

(21) Appl. No.: 11/855,999

(22) Filed: Sep. 14, 2007

(65) Prior Publication Data

US 2009/0071257 A1    Mar. 19, 2009

(51) Int. Cl.
*G01L 19/04*    (2006.01)
(52) U.S. Cl. ......................................... 73/708
(58) Field of Classification Search ................. 73/708
See application file for complete search history.

(56) References Cited

U.S. PATENT DOCUMENTS

| | | | |
|---|---|---|---|
| 5,454,426 A * | 10/1995 | Moseley | 165/136 |
| 6,170,337 B1 | 1/2001 | Zeman et al. | |
| 6,907,791 B2 | 6/2005 | Choe et al. | |
| 7,036,236 B1 | 5/2006 | Drescher et al. | |
| 2003/0114946 A1 * | 6/2003 | Kitchen | 700/97 |
| 2004/0084509 A1 | 5/2004 | Meyer et al. | |
| 2007/0125489 A1 | 6/2007 | Paul et al. | |

OTHER PUBLICATIONS

American Society of Mechanical Engineers; United States and Canada, Information and Procedures for Obtaining ASME Boiler and Pressure Vessel Certificates of Authorization and Code Symbol Stamps Under Sections I, IV, VII Div. 2, VII Div. 3, X, and XII; Codes & Standards Conformity Assessment; American Society of Mechanical Engineers; New York, NY; USA (Enclosed-ASME Certification Application.pdf).
American Society of Mechanical Engineers; ASME Boiler & Pressure Vessel Code Requirements; ASME B&PV Code Section VIII, Divisiion I; American Society of Mechanical Engineers; New York, NY; USA (Portions enclosed-ASME-IDS.pdf).
http://en.wikipedia.org/wiki/Creep_%28deformation%29 (Enclosed-CreepWiki.pdf).

(Continued)

*Primary Examiner*—Andre J Allen
(74) *Attorney, Agent, or Firm*—William B. Richards, Esq.; The Richards Law Firm

(57) ABSTRACT

A method for determining the maximum allowable working pressure of a microchannel device, particularly a diffusion-bonded, shim-based microchannel device operating at a temperature greater to or equal to a base material threshold temperature where significant creep may predominate, and when employing non-traditional materials of construction, when non-traditional fabrication or joining methods are used, or when spurious artifacts arise.

25 Claims, 14 Drawing Sheets

OTHER PUBLICATIONS http://www.heatric.com/ (Enclosed-Heatric.pdf).

Paul; Micro Energy and Chemical Systems (MECS) and Multiscale Fabrication; Nano/Micro Fabrication Facility, Oregon State University (Enclosed-Paul.pdf).

http://ec.europa.eu/enterprise/pressure_equipment/ped/index_en.html (Enclosed-PED.pdf, Sep. 18, 2007).

http://www.rpi.edu/dept/materials/COURSES/NANO/noseda/page2.html (Enclosed-RPICreep.pdf).

http://www.rpi.edu/dept/materials/COURSES/NANO/noseda/page2.html (Enclosed-UCBerkleyCreep.pdf).

Vamadevan; Process-Structure-Property Relationship of Micro-Channel Tube for CO(2) Climate Control Systems; Master's Thesis; Nov. 2004; Ohio University; Athens, Ohio (Enclosed-Vamadevan.pdf).

Wattanutchariya, et al.; Bonding fixture tolereance for high-volume metal microlamination based on fin buckling and laminae misalignment behavior; journal article; Precision Engineering 28 (2004) 117-128 (Enclosed-Wattanutchariya.pdf).

Wattanutchariya, et al.; Effect of Fixture Compliance on Thermally Enhanced Edge Registration in Microlamination; journal article; Journal of Manufacturing Science and Engineering 126 (Nov. 2004) 845-848 (Enclosed-Wattanutchariya2.pdf).

Wattanutchariya, et al.; Effect of Machining Methods on Flow Friction Behavior in Microchannels (Enclosed-Wattanutchariya3.pdf).

Wilson, et al.; Microchannel Devices; DOE-ARC-2001-011; U.S. Department of Energy, Albany Research Center; Albany, Oregon (Enclosed-Wilson.pdf).

* cited by examiner

```
┌─────────────────────────────────────────────────┐
│  HEAT REPRESENTATIVE BURST TEST DEVICE AT       │
│  CONSTANT RATE TO SECOND STATE TEMPERATURE      │
└─────────────────────────────────────────────────┘
                        │
                        │
          ┌─────────────────────────────┐
          │  HOLD REPRESENTATIVE BURST TEST │
          │  DEVICE AT SECOND STATE TEMPERATURE │
          └─────────────────────────────┘
                        │
                        │
┌─────────────────────────────────────────────────┐
│ PRESSURIZE REPRESENTATIVE BURST TEST DEVICE     │
│ AT CONSTANT RATE TO EXCESS PRESSURE             │
└─────────────────────────────────────────────────┘
```

Fig. 14

PRESSURE VESSEL TESTING

CROSS-REFERENCES TO RELATED APPLICATIONS (Not Applicable)

STATEMENT REGARDING FEDERALLY-SPONSORED RESEARCH AND DEVELOPMENT (Not Applicable)

BACKGROUND OF THE INVENTION

1. Field of the Invention

This invention relates generally to microchannel pressure vessels. Specifically, this invention relates to maximum allowable working pressure determination and pressure vessel certification of diffusion-bonded microchannel heat exchangers and microchannel heat exchanger/reactor combinations operating at higher temperatures.

2. Description of Related Art

Pressure vessel certification organizations, such as the American Society of Mechanical Engineers (ASME), establish rules of safety governing the design, fabrication, and inspection of boilers and pressure vessels. Other pressure vessel certification organizations include the European Commission through its Pressure Equipment Directive (PED), the Japanese Industrial Standards Committee which coordinates the standardization process of creating the Japanese Industrial Standards (JIS) which are then published by the Japanese Standards Association, and the International Organization for Standardization (ISO) which is developing ISO 16528. For example, the International Boiler and Pressure Vessel Code, published by the ASME, provides the procedures to follow to become accredited to certify products comply with the Code. Accreditation packages include the use of, for example, ASME Code Symbol Stamps such as the so-called "U" stamp for pressure vessels. To meet the requirements of the Code, the strength of the vessel may be computed based upon established formulas or hydrostatic tests which determine the maximum allowable working pressure (MAWP).

Many factors must be considered in MAWP determinations, such as the basic materials of construction (e.g., 10xx carbon steel, type 316L stainless as well as other steels, nickel alloy 617 as well as other nickel alloys, aluminum, titanium, platinum, rhodium, copper, chromium, brass, alloys of the foregoing materials, polymers; such as thermoset resins, ceramics, glass, polymer/fiberglass composites, quartz, silicon, or combinations thereof), methods of preparing construction components (e.g., stamping, photochemical etching or machining, electrodischarge machining, laser cutting, drilling and milling), methods of joining (e.g., welding, brazing, diffusion bonding, soldering, and adhesives), the design and various cross-sections of the vessel, the pressure and temperature regimes experienced by the vessel, not only during normal operating conditions, but during startup and shutdown, and the presence or absence of spurious artifacts.

When the MAWP cannot be satisfactorily determined using established methods, however, especially when employing non-traditional materials of construction, when higher temperatures are expected, particularly when those higher temperatures may cause significant creep, when non-traditional fabrication or joining methods are used, and, more particularly, when spurious artifacts arise, other methods must be employed. There exists then, a need for a method to determine MAWP and meet certification standards when employing higher temperatures, particularly when creep may be significant, when using non-traditional materials of construction, non-traditional component fabrication and joining methods, when fabrication-related artifacts arise, or combinations thereof.

BRIEF DESCRIPTION OF THE INVENTION

It is an object of an exemplary embodiment to provide a method of determining a maximum allowable working pressure (MAWP) of a pressure device.

It is a further object of an exemplary embodiment to provide a method of meeting certification requirements for pressure vessels.

It is a further object of an exemplary embodiment to provide a method for meeting certification requirements for pressure vessels fabricated with non-traditional fabrication methods.

It is a further object of an exemplary embodiment to provide a method of determining an MAWP of a microchannel device comprising a plurality of shims formed by stamping.

It is a further object of an exemplary embodiment to provide a method for meeting certification requirements for pressure vessels joined with non-traditional joining methods.

It is a further object of an exemplary embodiment to provide a method of determining an MAWP of a microchannel device joined by diffusion bonding.

It is a further object of an exemplary embodiment to provide a method of determining an MAWP of a microchannel device.

It is a further object of an exemplary embodiment to provide a method of determining an MAWP of a microchannel device comprising a plurality of shims.

It is a further object of an exemplary embodiment to provide a method of determining an MAWP of a microchannel device operating at or above a creep threshold temperature.

It is a further object of an exemplary embodiment to provide a method of determining an MAWP of a microchannel device where a property for a joined material at a room temperature is not superior or equal to that property for the base material at that room temperature.

It is a further object of an exemplary embodiment to provide a method of determining an MAWP of a microchannel device where a property for a joined material at a design temperature is not superior or equal to that property for the base material at that design temperature.

It is a further object of an exemplary embodiment to provide a method of determining an MAWP of a microchannel device containing spurious artifacts whose affects on MAWP are not calculable.

It is a further object of an exemplary embodiment to provide a method of burst testing a device.

It is a further object of an exemplary embodiment to provide a method of burst testing a device by independently increasing temperature and pressure from a first state to a second state, where the second state comprises a temperature greater than or equal to a base material creep threshold temperature.

Further objects of exemplary embodiments will be made apparent in the following Description of the Invention and the appended claims.

A method is disclosed for determining the maximum allowable working pressure (MAWP) for microchannel pressure vessels and particularly for microchannel pressure vessels fabricated from stamped Inconel® (Special Metals Corporation, New Hartford, N.Y.) alloy 617 shims with diffusion bonding, for which established calculations or certification procedures may be inapplicable. In addition, special considerations may be necessary when operating temperatures are high, for example, where creep becomes significant, such as at temperatures at or above about one-half the absolute melting point of the material, or when fabrication-related artifacts may be present in the finished vessel.

If properties and calculations for a base material of construction itself are not known, one may first test the base material alone considering various operating conditions, including startup, normal operation, and both normal and emergency shutdown. Although the base material of construction may be tested, in practice, the vessels themselves are constructed, or joined together, using various methods. To account for this, selected joining methods are covered in the published code materials. Thus, if the properties of the base material are known or established, and the joining method is prescribed and approved, it may be possible to use published computational methods to meet the applicable requirements for certification.

In most cases, the base material properties are, in fact, known. Even so, when the joined material properties are known, however, prescribed and approved certification procedures may not be applicable. In such cases, it may be possible to obtain joined material properties such as tensile strengths, toughness, creep, fatigue life, and fatigue strength using traditional testing methods. Such tests generally involve preparing specimens which are then subjected to the appropriate tests. With complex pressure vessels such as microchannel devices fabricated from, for example, alloy 617, with non-traditional joining methods such as, for example, diffusion bonding, even the resultant joined material properties may not be representative of the final finished device due, at least in part, to operating temperatures above the creep threshold temperature and artifacts inherent in the overall fabrication process. When this happens, complex, but representative, burst tests must be designed and performed. In the instant case, such tests include variations of temperature, pressure, rates of increase, and time.

If the temperatures of interest are above the creep threshold temperature and the joined material properties at either low temperatures (below significant creep range) or high temperatures (above significant creep range) are inferior to those properties for the conventional base material, however, neither prescribed certification calculations nor prescribed burst test procedures may be satisfactory. Particularized burst test procedures may burst test procedures may be satisfactory. Particularized burst test procedures may be required to receive certification approval.

The presence or absence of artifacts which arise from fabrication of vessel elements, for example, shims or plates for microchannel devices, or which arise from joining of vessel elements, for example, diffusion bonding shims to create a microchannel device, may also affect the MAWP and the certification procedure. For example, the presence of such artifacts may mandate a burst test certification procedure instead of utilizing prescribed certification calculations.

In the event the fabricated material properties are not comparable to those of the base material and the joining method is not included within published certification methodologies, or, the tested joined material properties are not believed to be representative, further testing may be required, including, for example, actual burst testing of representative devices.

In one exemplary embodiment, a method is provided for determining the MAWP of a microchannel device comprising a plurality of shims comprising a base material and joined with at least one microchannel fabrication technique. In an exemplary embodiment, a determination is made whether a condition of a device operating temperature is greater than or equal to a base material threshold temperature ($T_{Threshold}$) is true or false. If the condition of the device operating temperature is greater than or equal to $T_{Threshold}$ is true, then a determination is made of whether a condition of an at least first material property at a low temperature for a specimen of joined material is superior or equal to the at least first material property at the low temperature for a specimen of base material is true or false. If the condition of the at least first material property at a low temperature for a specimen of joined material is superior or equal to the at least first material property at the low temperature for a specimen of base material is false, then at least one burst test of at least one representative burst test device is conducted. If the condition of the at least first material property at a low temperature for a specimen of joined material is superior or equal to the at least first material property at the low temperature for a specimen of base material is true, then a determination is made of whether a condition of an at least first material property at a design temperature for a specimen of joined material is superior or equal to the at least first material property at the design temperature for a specimen of base material is true or false. If the condition of an at least first material property at a design temperature for a specimen of joined material is superior or equal to the at least first material property at the design temperature for a specimen of base material is false, then at least one burst test of at least one representative burst test device is conducted. If the condition of an at least first material property at a design temperature for a specimen of joined material is superior or equal to the at least first material property at the design temperature for a specimen of base material is true, then a determination is made of whether a condition of the presence of at least one spurious artifact is true or false. If the condition of the presence of at least one spurious artifact is true, then a determination is made whether a condition of at least one effect of at least one spurious artifact on MAWP at the design temperature is calculable is true or false. If the condition of at least one effect of at least one spurious artifact on MAWP at the design temperature is calculable is false, then at least one burst test of at least one representative burst test device is conducted.

In a further exemplary embodiment, the method further includes determining the device operating temperature.

In a further exemplary embodiment, the method further includes selecting the device operating temperature as one of: the normal operating temperature, the maximum temperature caused by random operational perturbations, the maximum temperatures caused by operational changes, the maximum startup temperature, and the maximum shutdown temperature.

In a further exemplary embodiment, wherein the device comprises a steam methane reformer, the method further includes selecting the device operating temperature from between about 800 deg. C. and about 1200 deg. C.

In a further exemplary embodiment, the method further includes selecting the device temperature from between about 800 deg. C. and about 950 deg. C.

In a further exemplary embodiment, the base material is a nickel alloy containing at least 35 percent nickel.

In a further exemplary embodiment, the nickel alloy contains at least 60 percent nickel.

In a further exemplary embodiment, the base material is alloy 617.

In a further exemplary embodiment, the method further includes determining $T_{Threshold}$.

In a further exemplary embodiment, the method further includes selecting $T_{Threshold}$ as $0.5*T_{MP}$, where $T_{MP}$=the absolute melting point of the base material.

In a further exemplary embodiment, the method further includes calculating $T_{Threshold}$ as between about 530 deg. C. and about 552 deg. C.

In a further exemplary embodiment, the method further includes selecting $T_{Threshold}$ as $0.3*T_{MP}$, where $T_{MP}$=the absolute melting point of the base material.

In a further exemplary embodiment, wherein the base material is alloy 617, the method further includes calculating $T_{Threshold}$ as between about 209 deg. C. and about 220 deg. C.

In a further exemplary embodiment, the method further includes selecting $T_{Threshold}$ as the temperature at which a base material creep predominates.

In a further exemplary embodiment, the method further includes selecting $T_{Threshold}$ as the temperature at which a base material creep stress limit becomes less than a base material tensile limit.

In a further exemplary embodiment, the base material creep stress limit is 80 percent of the minimum stress which causes rupture at the end of about 100,000 hours.

In a further exemplary embodiment, the base material creep rate stress limit is 100 percent of the average stress which causes a creep rate of about 0.01 percent per 1,000 hours.

In a further exemplary embodiment, the base material tensile limit is about the tensile strength divided by 3.5.

In a further exemplary embodiment, wherein the base material is alloy 617, the method further includes selecting $T_{Threshold}$ as between about 625 deg. C. and about 710 deg. C.

In a further exemplary embodiment, the method further includes selecting $T_{Threshold}$ as the temperature at which a base material creep stress limit becomes less than a base material yield limit.

In a further exemplary embodiment, the base material yield limit is about two-thirds the yield stress.

In a further exemplary embodiment, the method further includes selecting the at least first material property from the group consisting of ultimate tensile strength, yield strength, yield tensile strength, percent elongation at failure, or combinations thereof.

In a further exemplary embodiment, the method further includes selecting the low temperature as less than $T_{Threshold}$ and about room temperature.

In a further exemplary embodiment, the method further includes selecting the design temperature as greater than or equal to the device operating temperature.

In a further exemplary embodiment, the method further includes selecting the design temperature as the operating temperature in deg. C. plus about less than 50 deg. C.

In a further exemplary embodiment, the device is a microchannel reactor and the at least one representative burst test device is representative of the device with respect to channel dimensions including, but not limited to, height, width, length, or combinations thereof; fabrication methods, including, but not limited to, stamping, bonding, including, but not limited to diffusion bonding, considering, but not limited to, method, time, temperature, pressure, or combinations thereof; surface preparation, including, but not limited to, finish, passivation, etching, cleaning, coating, flatness, lay, waviness, or combinations thereof; wall thicknesses; base material, including, but not limited to, alloy 617; rib dimensions; heat treat cycles; heating cycles during manufacture; shim thickness; symmetry; size scale; or combinations thereof.

In a further exemplary embodiment, the method further includes determining the presence of a stamp rollover, carbide precipitates, misalignment or offset of shim ribs, bowing of channel walls, grain size growth, or combinations thereof.

In a further exemplary embodiment, the method further includes comparing the size of a stamp rollover, carbide precipitates, misalignment or offset of shim ribs, shim thickness, bowing of channel walls, or grain size growth to channel size.

In a further exemplary embodiment, the method further includes determining the presence of grain size growth relative to shim thickness.

In a further exemplary embodiment, a method is provided for burst testing a representative device. In an exemplary embodiment, the device is hearted at a substantially constant rate from a first state temperature to a second state temperature, the second state temperature greater than or equal to a base material threshold temperature and allowed to thermally equilibrate. The device is then held at the second state temperature while being pressurized at a substantially constant rate from a first state pressure to a second state pressure. Finally the device is held at substantially the second state temperature and substantially the second state pressure for a fixed period of time.

In a further exemplary embodiment, the method further includes pressurizing the device with preheated gas.

In a further exemplary embodiment, the method includes the second state temperature greater than about a design temperature.

In a further exemplary embodiment, the method includes the second state pressure greater than about a threshold temperature.

In a further exemplary embodiment, the second state temperature is greater than about 30 bar.

In a further exemplary embodiment, the constant rate of heating is selected to avoid significant creep.

In a further exemplary embodiment, the constant rate of heating is between about one deg. C. per minute and about ten deg. C. per minute.

In a further exemplary embodiment, the second state temperature is greater than about 900 deg. C.

In a further exemplary embodiment, the constant rate of pressurizing is between about one bar per minute and about ten bar per minute.

In a further exemplary embodiment, a method is provided for burst testing a representative device. In an exemplary embodiment, the device is pressurized at a substantially constant rate from a first state pressure to a second state pressure and held for a fixed period of time. The device is then held at the second state pressure while being heated at a substantially constant rate from a first state temperature to failure.

In a further exemplary embodiment, the second state pressure is greater than about 30 bar.

In a further exemplary embodiment, the constant rate of pressurizing is between about one bar and about ten bar per minute.

In a further exemplary embodiment, the constant rate of heating is between about one deg. C. and about ten deg. C. per minute.

In a further exemplary embodiment, a method is provided for burst testing a representative device. In an exemplary embodiment, the device is heated at a substantially constant rate from a first state temperature to a second state temperature and allowed to thermally equilibrate. The device is then held at the second state temperature while being pressurized at a substantially constant rate from a first state pressure to an excess pressure.

In a further exemplary embodiment, the method includes a second state temperature about a design temperature.

In a further exemplary embodiment, the method includes the design temperature greater than about a threshold temperature.

In a further exemplary embodiment, the constant rate of heating is between about one deg. C. per minute and about ten deg. C. per minute.

In a further exemplary embodiment, the second state temperature is greater than about 900 deg. C.

In a further exemplary embodiment, the constant rate of pressurizing is between about one bar per minute and about ten bar per minute.

In a further exemplary embodiment, the method further includes pressurizing the representative burst test device to failure.

In a further exemplary embodiment, a method is provided for determining the MAWP of a microchannel device operating at a temperature greater to or equal to a base material threshold temperature ($T_{Threshold}$). In the exemplary embodiment, the microchannel device comprises a plurality of shims, the shims comprising a base material and the shims joined with at least one microchannel fabrication technique. The method comprises determining whether a first condition of an at least first material property at a low temperature for a specimen of joined material superior or equal to the at least first material property at the low temperature for a specimen of base material is true or false; conducting at least one burst test of at least one representative burst test device when the first condition is false, the burst test comprising independently increasing temperature and pressure of the at least one representative burst test device from a first state to a second state, the second state comprising a temperature greater than or equal to the base material threshold temperature; determining whether a second condition of an at least first material property at a design temperature for a specimen of joined material is superior or equal to the at least first material property at the design temperature for a specimen of base material is true or false when the first condition is true; conducting at least one burst test of at least one representative burst test device when the second condition is false, the burst test comprising independently increasing temperature and pressure of the at least one burst test device from a first state to a second state, the second state comprising a temperature greater than or equal to the base material threshold temperature; determining whether a third condition of the presence of at least one spurious artifact is true or false when the second condition; determining whether a fourth condition of at least one effect of at least one spurious artifact on MAWP at the design temperature is calculable is true or false when the third condition; and conducting at least one burst test of at least one representative burst test device when the fourth condition is false, the burst test comprising independently increasing temperature and pressure of the at least one burst test device from a first state to a second state, the second state comprising a temperature greater than or equal to the base material threshold temperature.

BRIEF DESCRIPTION OF THE DRAWINGS

FIG. 3b is an elevation view of the cross-section of FIG. 3a.

FIG. 4b is an elevation view of the cutaway cross-section of FIG. 4a.

FIG. 5b is an elevation view of the cutaway cross-section of FIG. 5a.

FIG. 14 is a flowchart illustrating an exemplary embodiment of the present invention comprising burst testing at constant temperature with increasing pressure.

Figure 1:
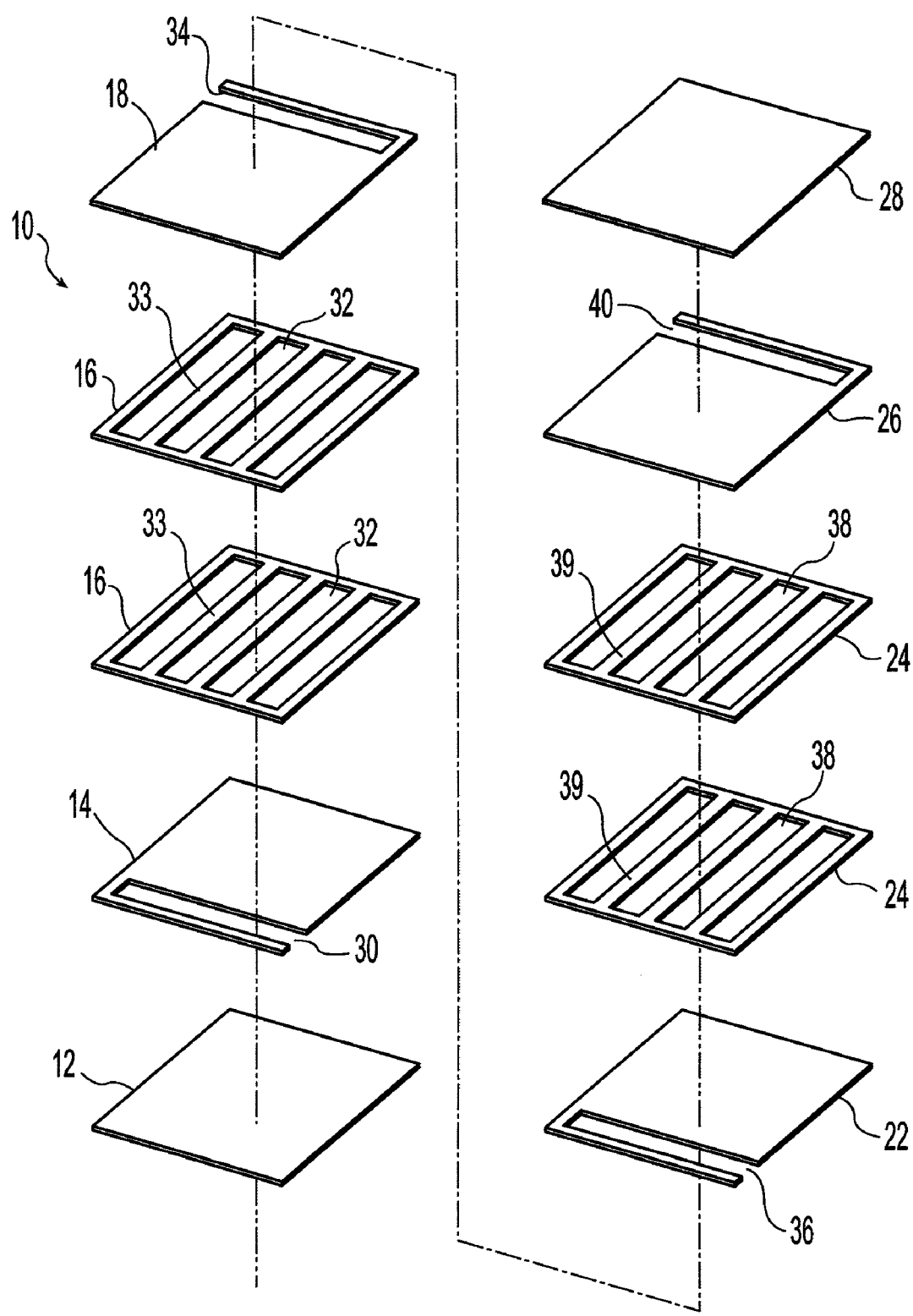
FIG. 1 is an exploded axonometric projection view of an exemplary microchannel device.
Figure 2:
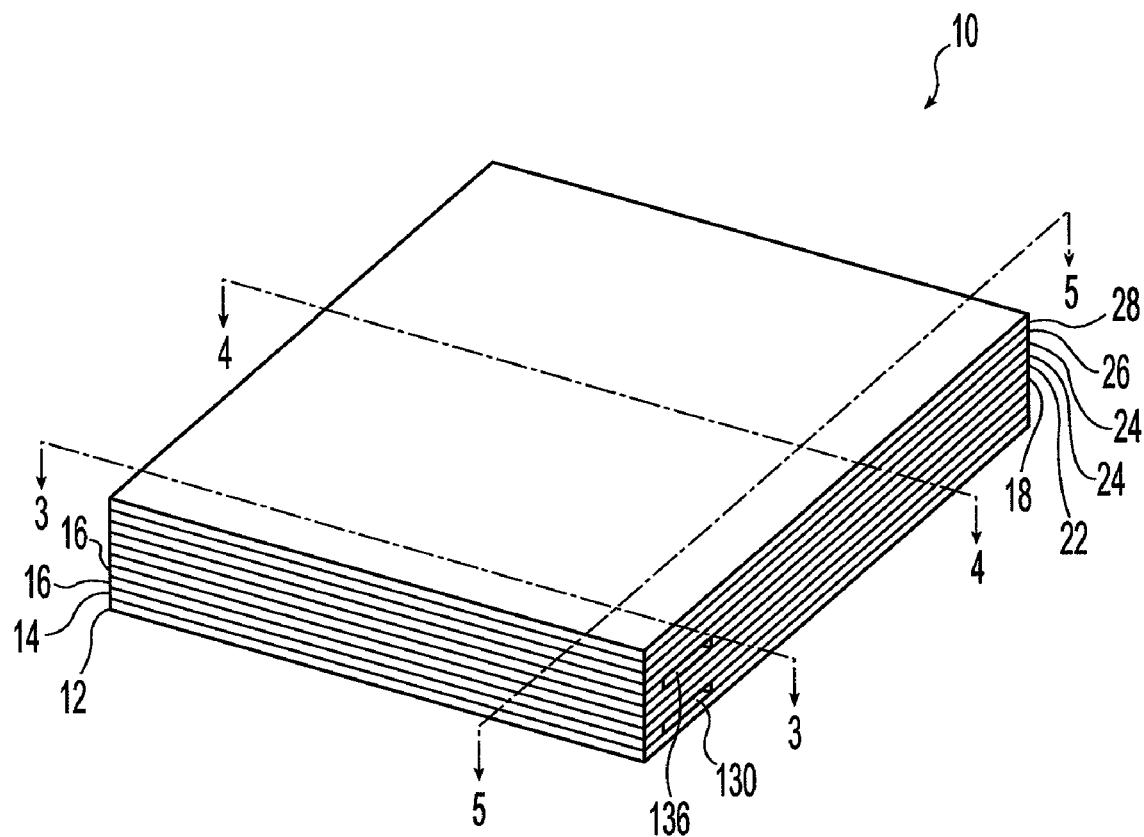
FIG. 2 is an axonometric projection view of the exemplary microchannel device illustrated in FIG. 1.
Figure 3A:
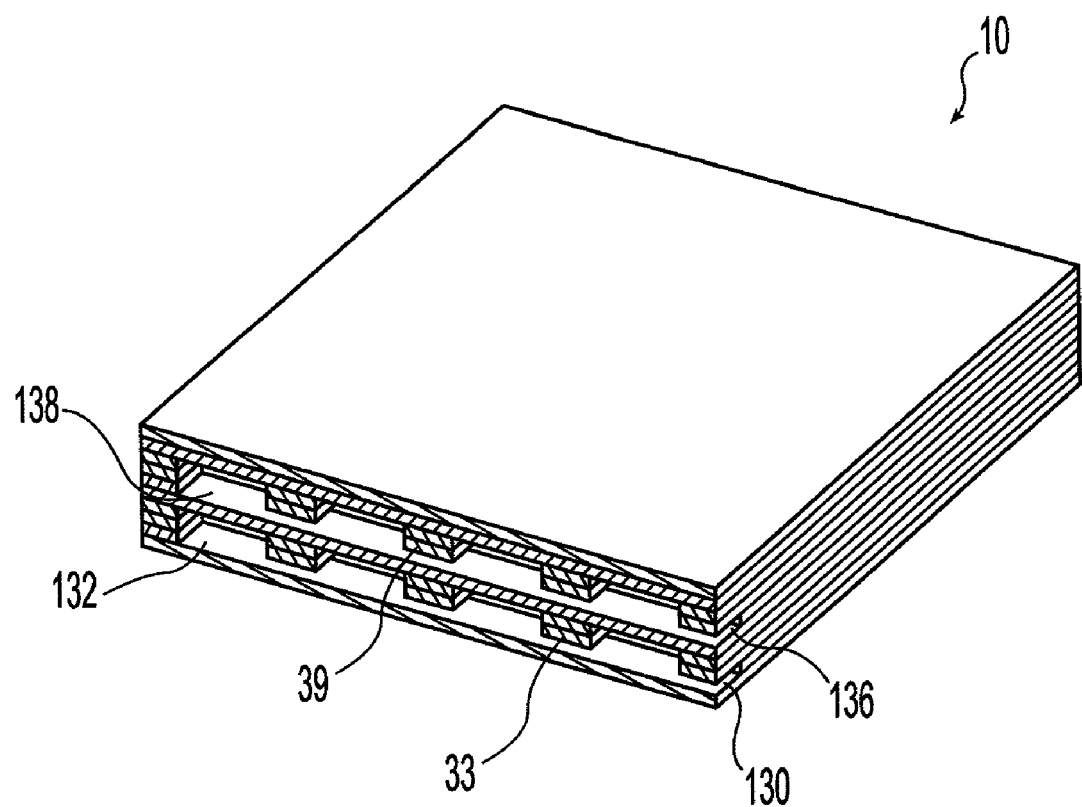
FIG. 3a is an axonometric projection view of a cross-section of the exemplary microchannel device along the line 3-3 in FIG. 2.
Figure 3B:
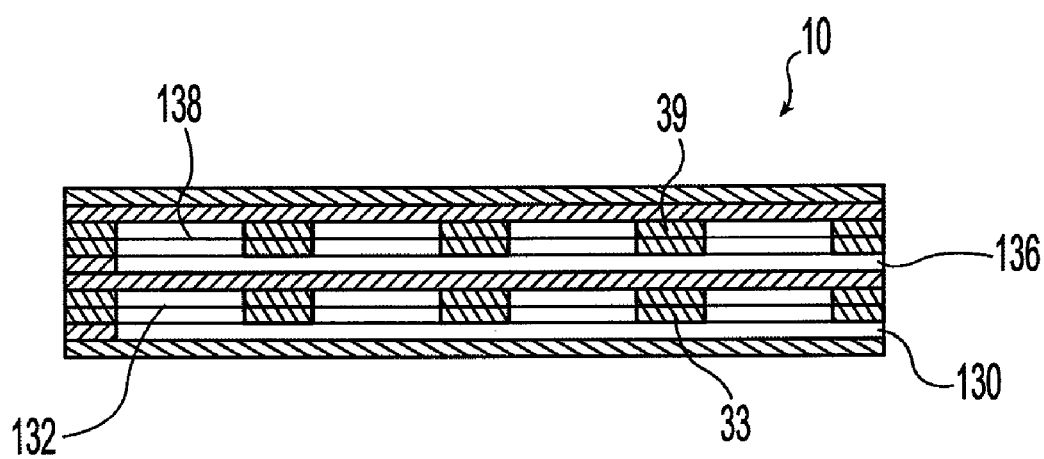
Figure 4A:
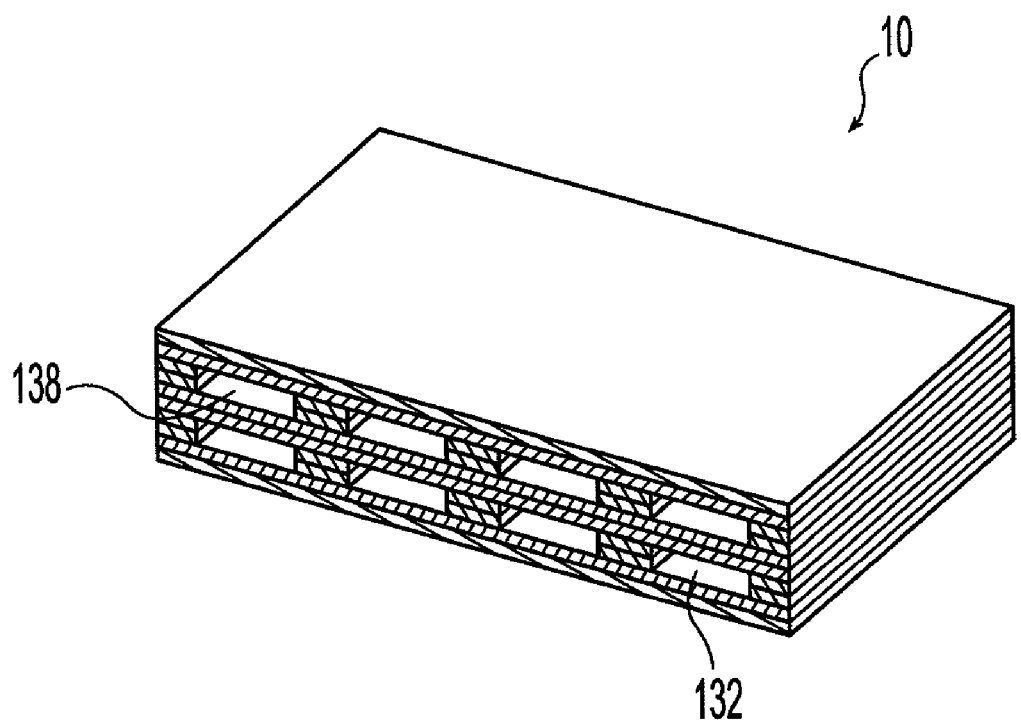
FIG. 4a is an axonometric projection view of a cross-section of the exemplary microchannel device along the line 4-4 in FIG. 2.
Figure 4B:
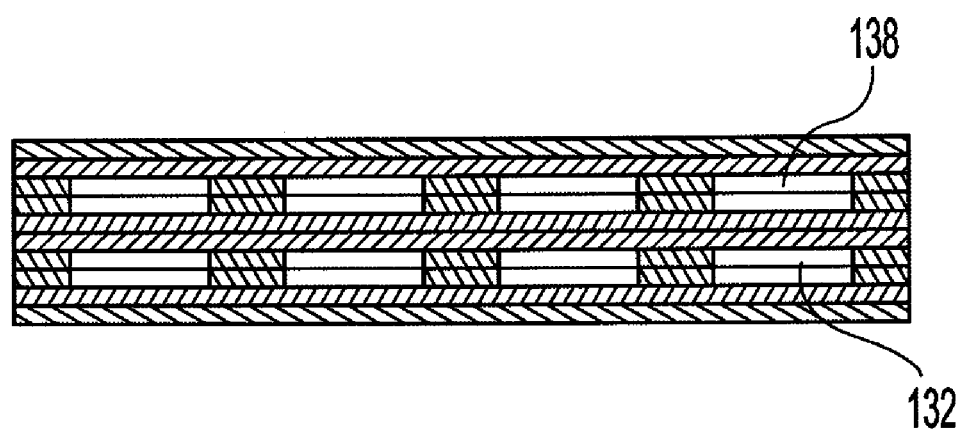
Figure 5A:
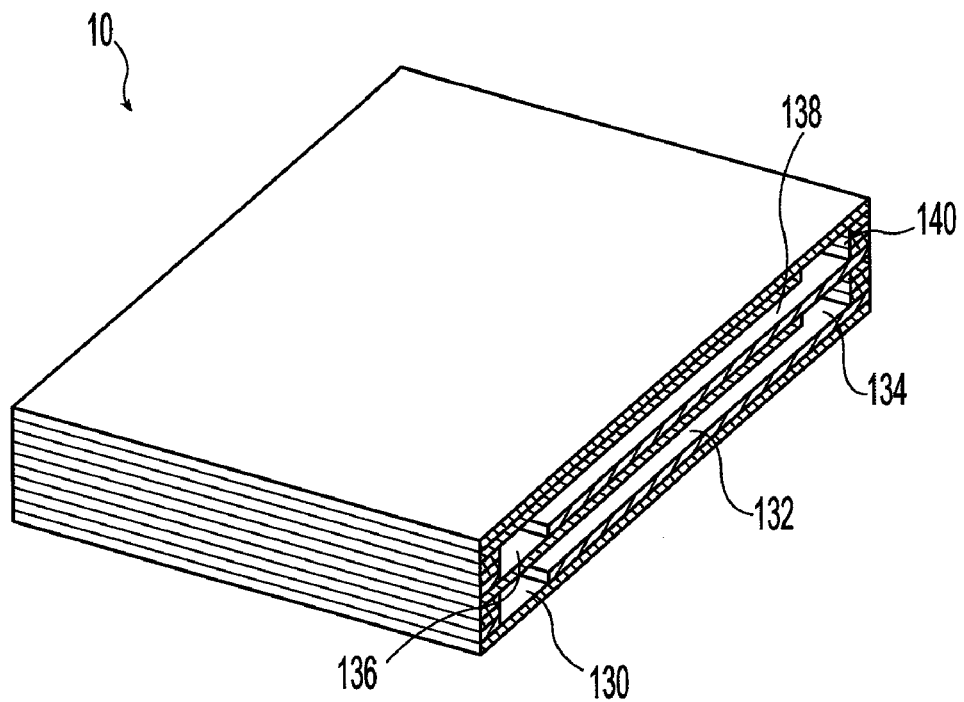
FIG. 5a is an axonometric projection view of a cross-section of the exemplary microchannel device along the line 5-5 in FIG. 2
Figure 5B:
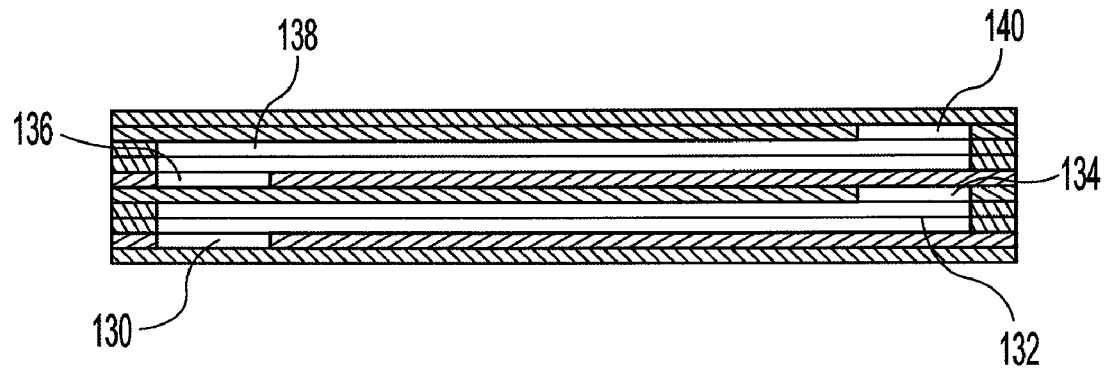

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

An exemplary microchannel device 10 is shown in FIGS. 1-5b. Turning first to FIG. 1, the exemplary microchannel device 10 is shown in an exploded axonometric projection view. The microchannel device 10 comprises a plurality of shims (e.g., 12, 14, 16) which cooperate to form a plurality of various features of the microchannel device 10. Shims generally refer to substantially planar plates or sheets that can have any width and height and preferably have a thickness (smallest dimension) of ten millimeters (mm) or less, and, in some preferred embodiments, between 50 and 1,000 microns (1 mm). The microchannel device 10 comprises a first end shim 12 which is a solid plate to partially enclose and define the microchannel device 10. Next is a first manifold shim 14 which includes a first manifold slot 30. Next is one or more first channel shims 16 which comprise a plurality of first ribs 33, which first ribs 33 at least partially define a plurality of first channel slots 32. As will be appreciated by those skilled in the relevant art, multiple first channel shims 16 may be provided to at least partially define the dimensions of a plurality of first channels 132 (e.g., FIGS. 3a-5b). The dimensions of the first manifold slot 30 may at least partially define the dimensions of a first manifold 130 (e.g., FIGS. 2-3b, 5a, and 5b). As will also be appreciated by those skilled in the relevant art, multiple first manifold shims 14 may be provided to at least partially define the dimensions of the first manifold 130. As will also be appreciated by those skilled in the relevant art, the first manifold 130 may, for example, enable the distribution of fluids entering the microchannel device 10 to the first channels 132. Next is a second manifold shim 18 which includes a second manifold slot 34 and the dimensions of the second manifold slot 34 at least partially define the dimensions of a second manifold 134 (e.g., FIGS. 2-3b, 5a, and 5b). As will be appreciated by those skilled in the relevant art, multiple second manifold shims 18 may be provided to at least partially define the dimensions of the second manifold 134. As will also be appreciated by those skilled in the art, the second manifold 134 may, for example, enable the collection of fluids exiting the microchannel device 10 from the first channels 132. Next is a third manifold shim 22 which includes a third manifold slot 36 and the dimensions of the third manifold slot 36 at least partially define the dimensions of a third manifold 136 (e.g., FIGS. 2-3b, 5a, and 5b). As will be appreciated by those skilled in the relevant art, multiple third manifold shims 22 may be provided to at least partially define the dimensions of the third manifold 136. Next is one or more second channel shims 24 which comprise a plurality of second ribs 39, which second ribs 39 at least partially define a plurality of second channel slots 38. As will be appreciated by those skilled in the relevant art, multiple second channel shims 24 may be provided to at least partially define the dimensions of a plurality of second channels 138 (e.g., FIGS. 3a-5b). As will also be appreciated by those skilled in the relevant art, the third manifold 136 may, for example, enable the discharge of fluids from the second channels 138. Next is a fourth manifold shim 26 which includes a fourth manifold slot 40 and the dimensions of the fourth manifold slot 40 at least partially define the dimensions of a fourth manifold 140 (e.g., FIGS. 5a and 5b). As will be appreciated by those skilled in the relevant art, multiple fourth manifold shims 26 may be provided to at least partially define the dimensions of the fourth manifold 140. As will be appreciated by those skilled in the art, the fourth manifold 140 may, for example, enable the distribution of fluids to the second channels 138. Finally, a second end shim 28 is provided to partially enclose and further define the microchannel device 10.

The microchannel device 10 may be a reactor and heat exchanger in combination. The microchannel device 10 may be designed or operated to conduct one or more chemical unit operations, including mixing, chemical reaction, heating, cooling, heat exchange, vaporization, condensation, distillation, absorption, adsorption, or solvent exchange. The shims (e.g., 12, 14, 16) comprise a base material which may comprise any material that provides sufficient strength, dimensional stability, and heat transfer characteristics to permit operation. These materials include steel, stainless steel (e.g., 304, 316) aluminum, titanium, nickel, platinum, rhodium, copper, chromium, brass, alloys of any of the foregoing metals (e.g., Inconel 617® (Special Metals), Haynes HR-120® (Haynes, Int'l., Inc., Kokomo, Ind.), Haynes HR-230® (Haynes Int'l.), Hastelloy® (Haynes Int'l.), Monel® (Special Metals), or oxidative dispersion-strengthened alloys), polymers (e.g., thermoset resins), ceramics, glass, composites comprising one or more polymers (e.g., thermoset resins) and fiberglass, quartz, silicon, or a combination of two or more thereof. These materials may be supplied in rolled form, cat, forged, or extruded. The components of the microchannel device 10 may be fabricated using known techniques including wire electrodischarge machining, conventional machining, laser cutting, photochemical machining, electrochemical machining, molding, water jet, stamping, etching (e.g., chemical, photochemical, or plasma etching), and combinations thereof. A stack of shims (e.g., 12, 14, 16) may be joined via diffusion bonding, laser welding, diffusion brazing, and similar methods to form an integrated device.

As will be appreciated by one skilled in the relevant art, a virtually limitless variety of microchannel devices are possible, most extremely complex, but which embody the basic features described herein.

Figure 11:
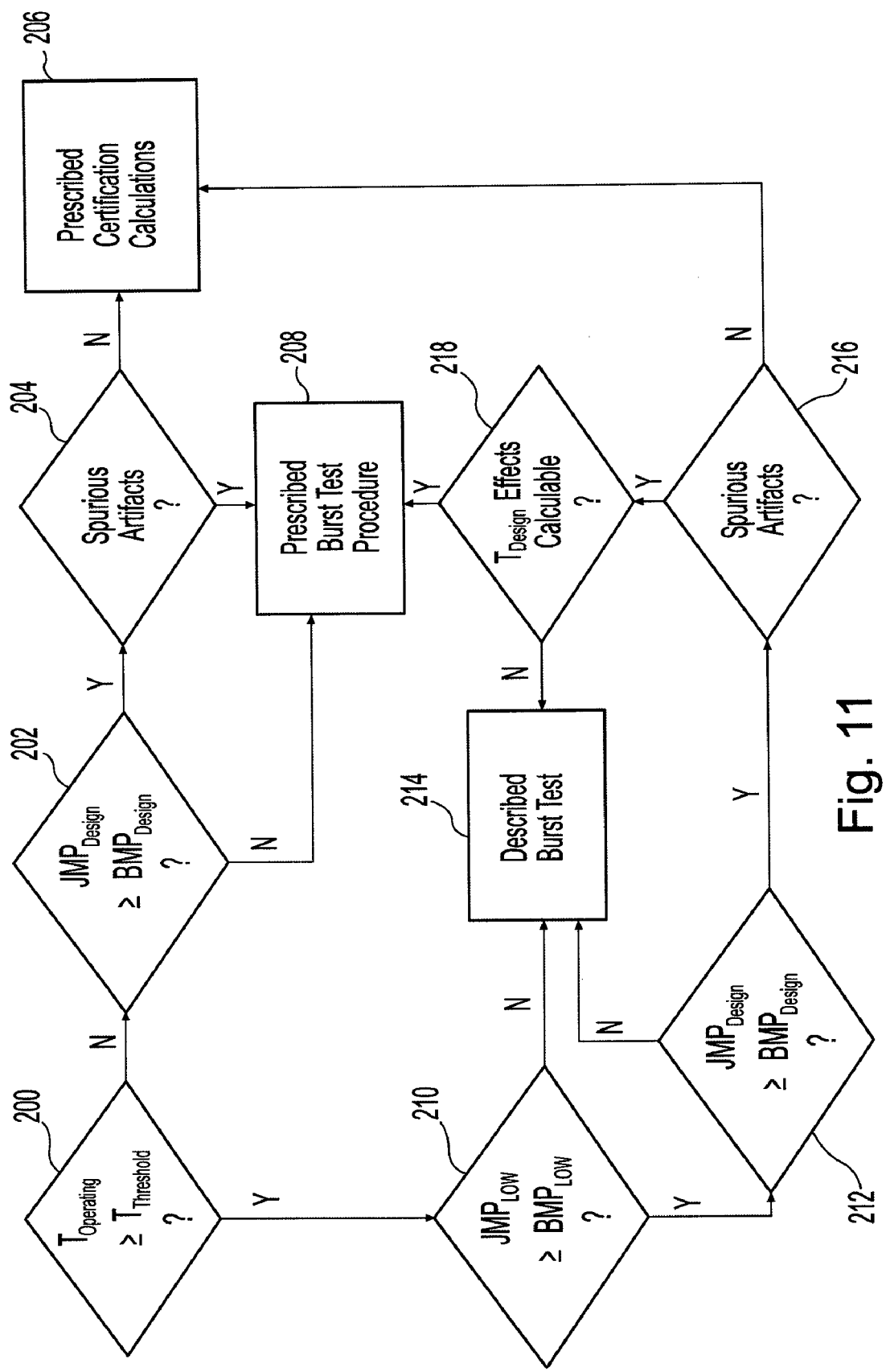
FIG. 11 is a flowchart illustrating an exemplary embodiment of the present invention comprising creep considerations.
Figure 12:
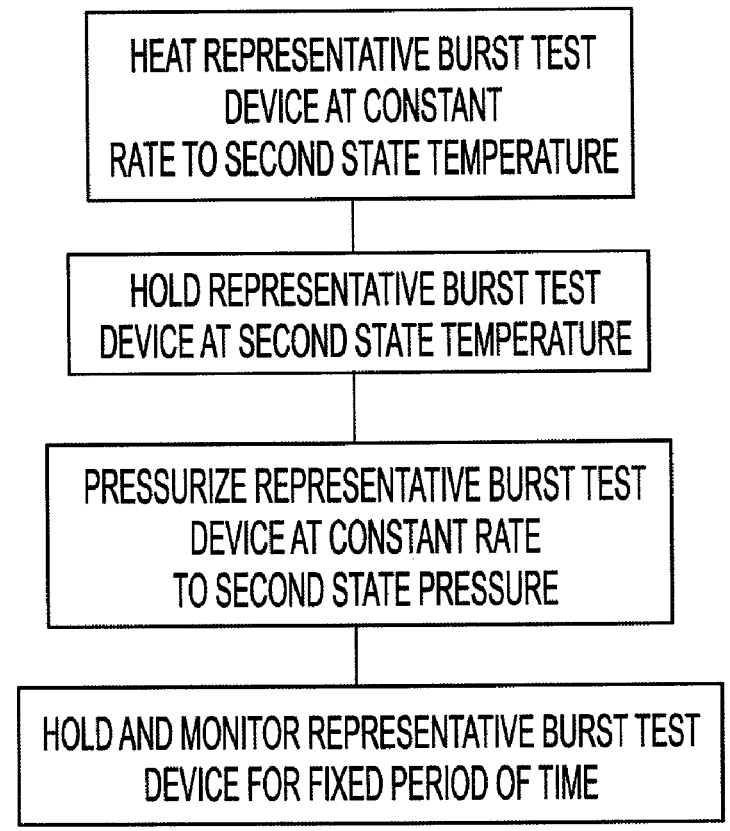
FIG. 12 is a flowchart illustrating an exemplary embodiment of the present invention comprising burst testing at constant temperature and pressure.
Figure 13:
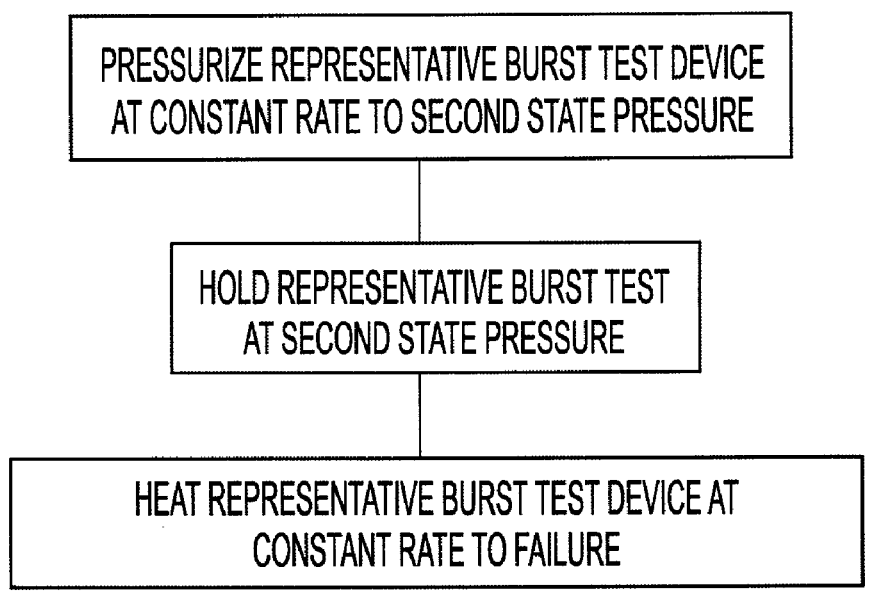
FIG. 13 is a flowchart illustrating an exemplary embodiment of the present invention comprising burst testing at constant pressure with increasing temperature.
Figure 15:
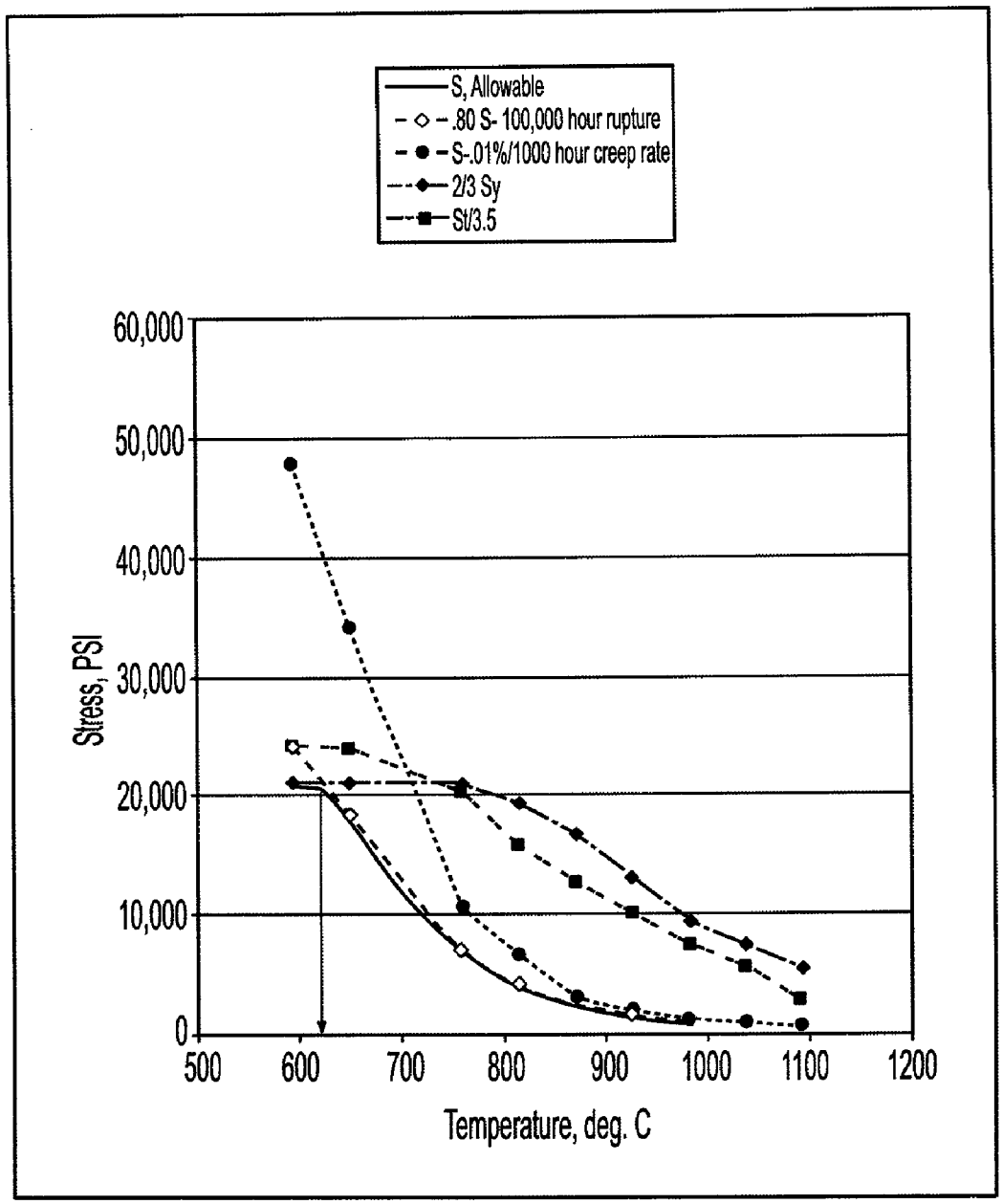
FIG. 15 is a graph illustrating various measures of stress versus temperature for an exemplary base material, alloy 617.
Figure 16:
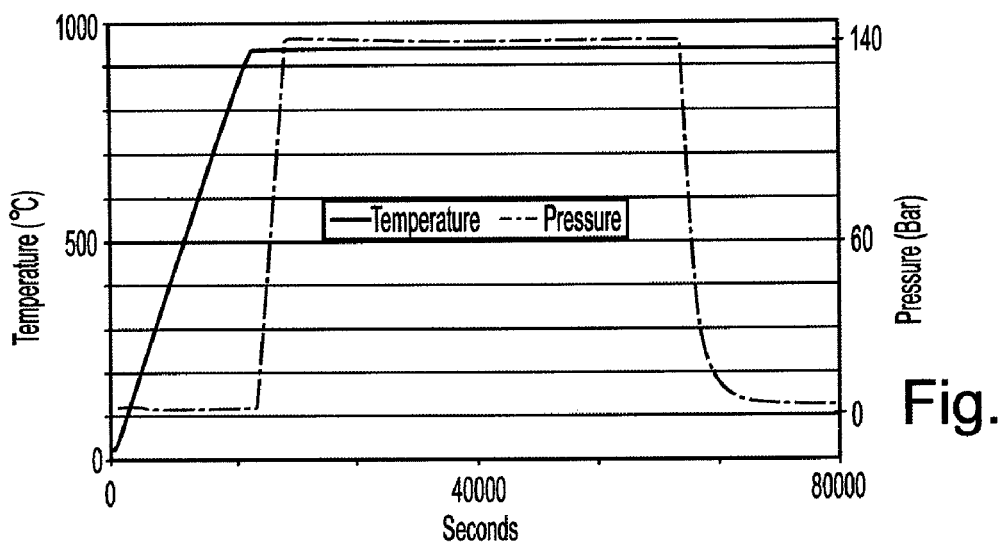
FIG. 16 is a graph illustrating the results of an exemplary burst test with temperature and pressure held constant.
Figure 17:
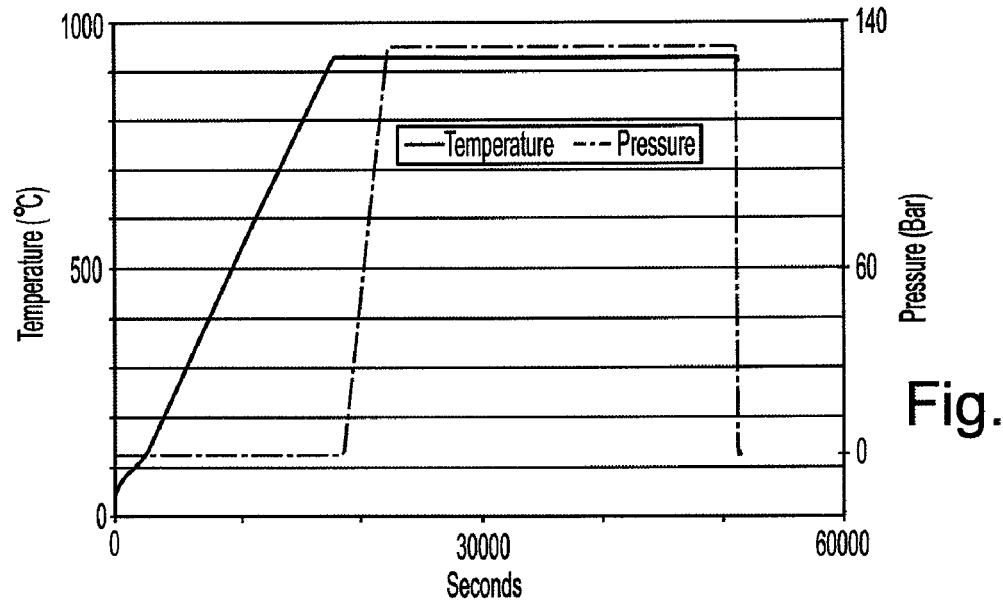
FIG. 17 is a graph illustrating the results of a further exemplary burst test with temperature and pressure held constant.
Figure 18:
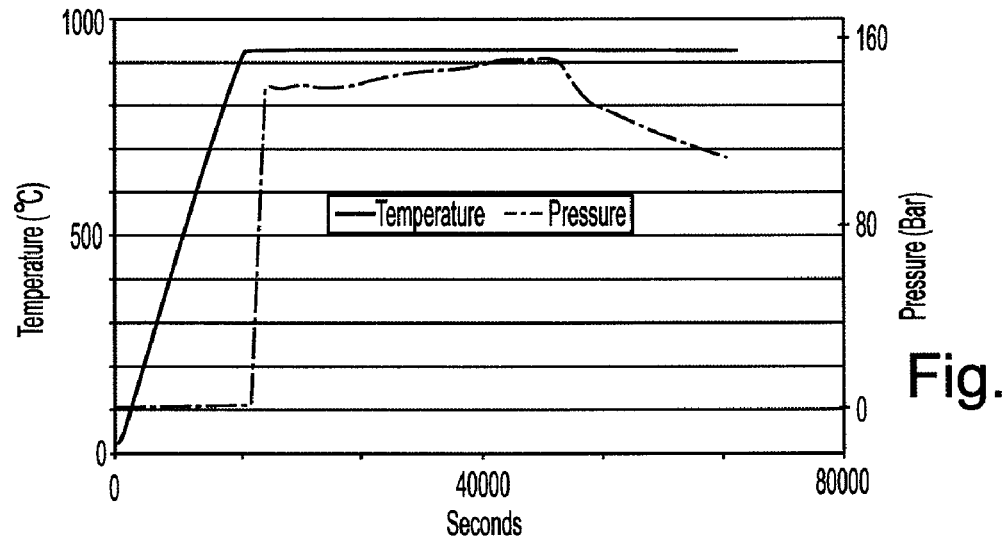
FIG. 18 is a graph illustrating the results of a further exemplary burst test with temperature and pressure held constant.
Figure 19:
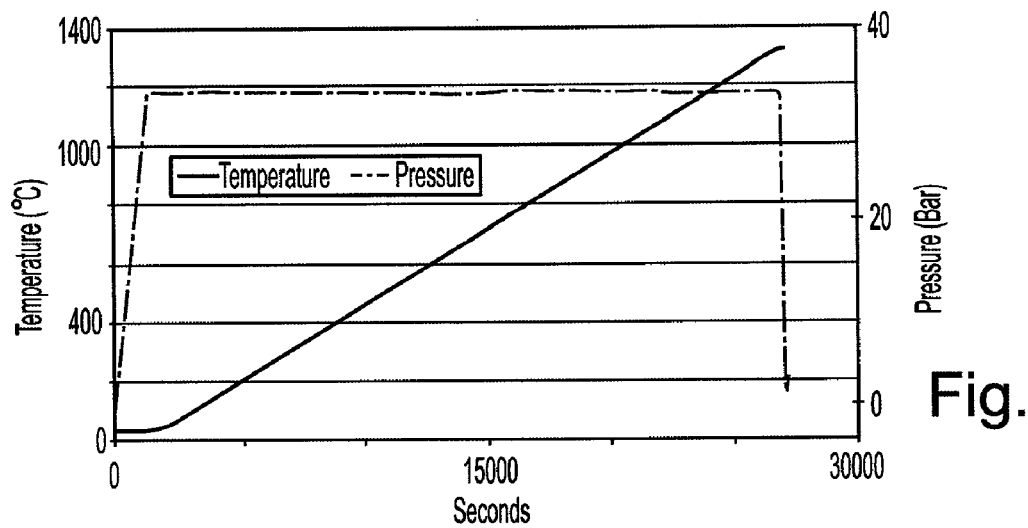
FIG. 19 is a graph illustrating the results of an exemplary burst test with constant pressure and increasing temperature.
Figure 20:
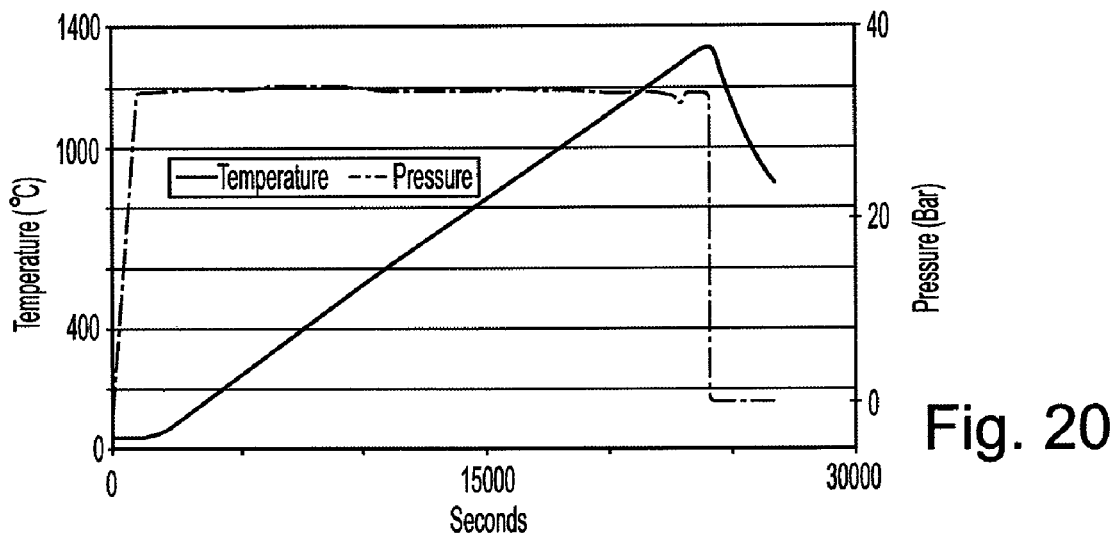
FIG. 20 is a graph illustrating the results of a further exemplary burst test with constant pressure and increasing temperature.
Figure 21:
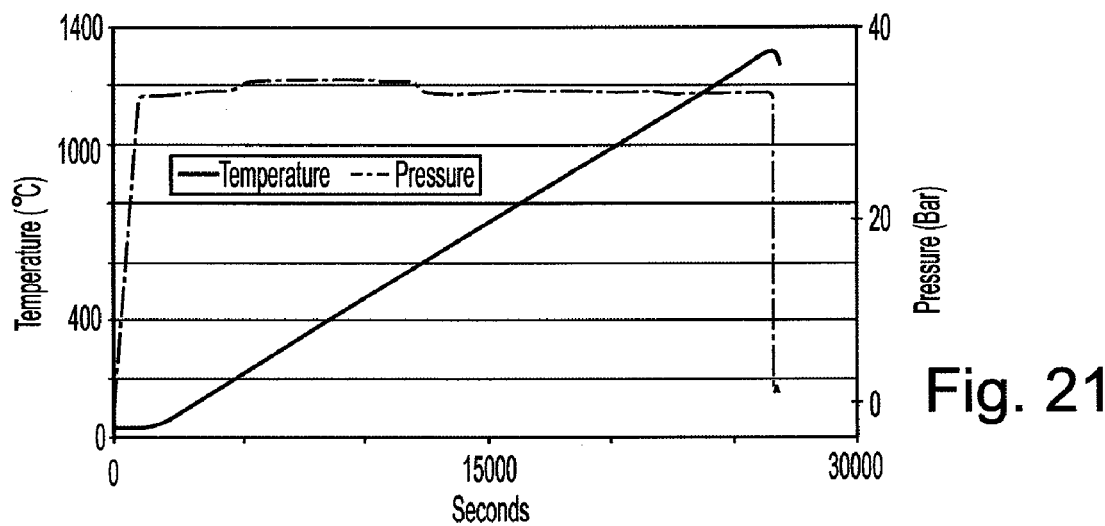
FIG. 21 is a graph illustrating the results of a further exemplary burst test with constant pressure and increasing temperature.
Figure 22:
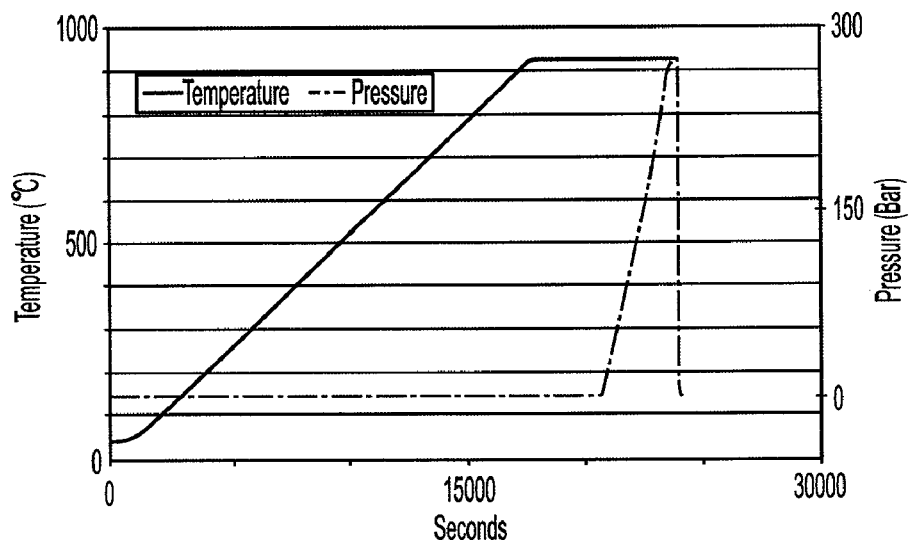
FIG. 22 is a graph illustrating the results of an exemplary burst test with constant temperature and increasing pressure.
Figure 23:
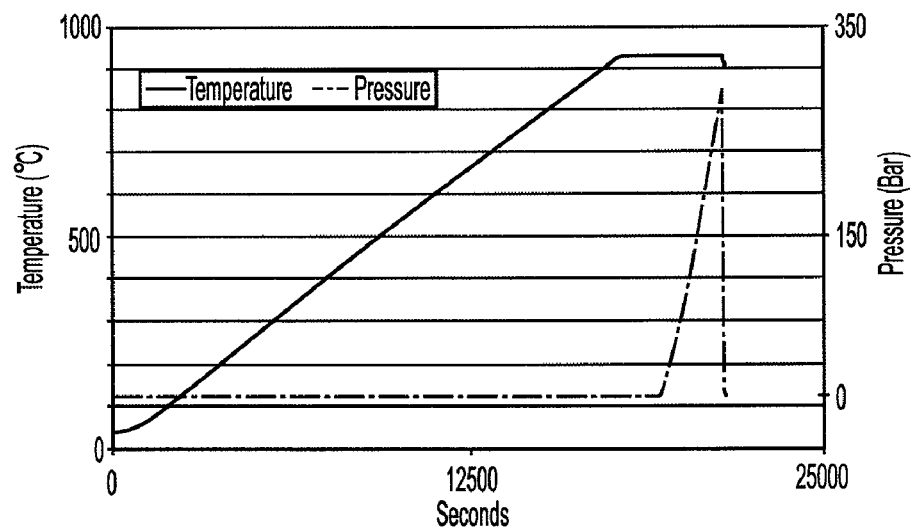
FIG. 23 is a graph illustrating the results of a further exemplary burst test with constant temperature and increasing pressure.
Figure 24:
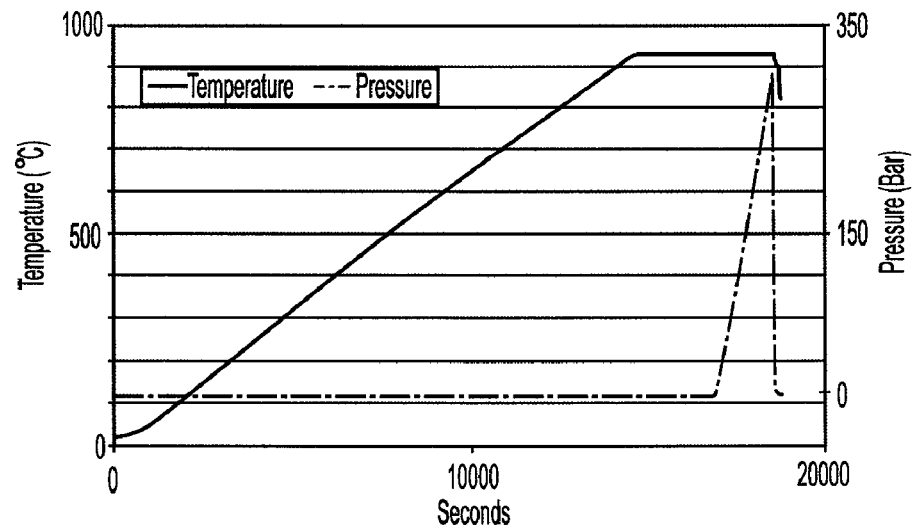
FIG. 24 is a graph illustrating the results of a further exemplary burst test with constant temperature and increasing pressure.

Turning now to FIG. 11, a method is shown for determining the MAWP of a pressure vessel, and particularly for a microchannel device. When entering at node 200, a determination is made as to whether an operating temperature ($T_{Operating}$) is greater than or equal to a threshold temperature ($T_{Threshold}$). $T_{Operating}$ is that temperature at which the device will operate during those operations of interest and which will present the conditions for which the MAWP must be determined. For example, $T_{Operating}$ might normally be selected at the normal operating temperature of the device under normal, sustained operation. Other considerations would include, for example, the maximum temperatures expected during normal startup or shutdown. Additionally, the maximum temperature expected from random operational perturbations or normal operational changes may be considered. As a selection, $T_{Operating}$ may be selected as the maximum of one of the above-mentioned temperatures. If, for example, the pressure vessel is a microchannel device and the microchannel device comprises a steam methane reformer, $T_{Operating}$ may be selected from between about 800 deg. C. to about 1200 deg. C. Additionally, $T_{Operating}$ may be selected from between about 800 deg. C. and about 950 deg. C. As will be appreciated by those skilled in the relevant art, $T_{Operating}$ will vary but will be easily and eminently determinable from the process being considered. $T_{Threshold}$ may be chosen as generally the lowest temperature at which the base material creep properties limit allowable stress over such base material properties as tensile stress or yield stress. $T_{Threshold}$ may be selected by comparing various limits for allowable stress set by considering engineering safety factors. One limit, for example, may be one-half the absolute melting point temperature of the base material. For example, when the base material is alloy 617, the base material melting point may vary somewhat (approximately 1,333 deg. C. to about 1,377 deg. C.). $T_{Threshold}$ may fall between about 530 deg. C. and about 552 deg. C. using this criterion. Alternatively, for example, $T_{Threshold}$ may be selected as about 0.3 times the absolute melting point of the base material. Thus, for a base material of alloy 617, $T_{Threshold}$ may fall between about 209 deg. C. and about 222 deg. C. $T_{Threshold}$ may, for example, be selected as the temperature at which a base material creep stress limit becomes less than a base material tensile stress limit or a base material yield stress limit. For example, the limit may be based upon the lowest temperature associated with one of the following criteria: (a) a base material creep stress limit of 80 percent of the minimum stress which causes rupture at the end of about 100,000 hours; (b) a base material creep rate stress limit about 100 percent of the average stress which causes a creep rate of about 0.01 percent per 1,000 hours, or (c) a base material tensile limit of about the tensile strength divided by 3.5. Turning to FIG. 15, for example, a base material of alloy 617 would show $T_{Threshold}$ of between about 625 deg. C. and about 710 deg. C. $T_{Threshold}$ may, for example, be selected at the temperature at which a base material creep stress limit becomes less than a base material yield limit. For example, when the base material yield limit is about two-thirds the yield stress limit. Turning to FIG. 15, for example, a base material of alloy 617 would show $T_{Threshold}$ of about 625 deg. C. As will be appreciated by those skilled in the relevant art, the base material may comprise, for example, a nickel alloy containing at least 35 percent nickel or at least 60 percent nickel.

Figure 6:
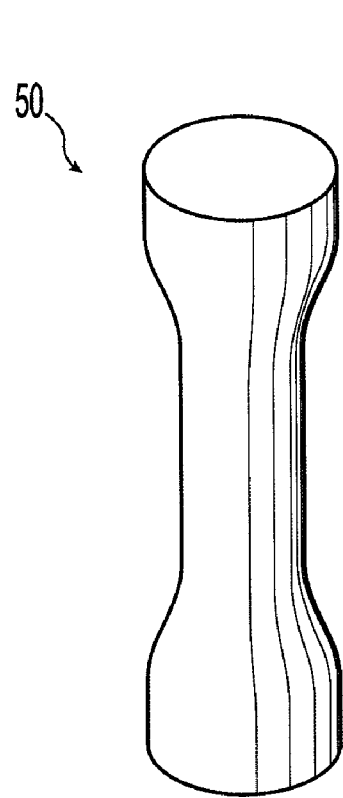
FIG. 6 is an illustration of a base material test specimen.
Figure 7:
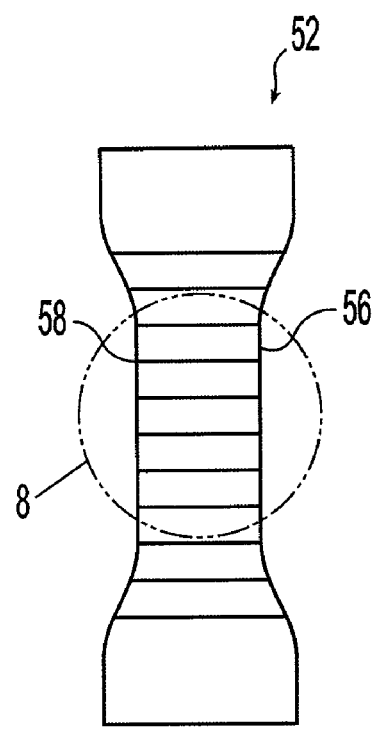
FIG. 7 is an illustration of a fabricated material test specimen.

Returning now to FIG. 11, node 202, if $T_{Operating}$ is not greater than or equal to $T_{Threshold}$ (node 200 is false), an at least one material property at a design temperature for joined material ($JMP_{Design}$) is compared with the at least one material property at a design temperature for the base material ($BMP_{Design}$). A typical base material test specimen 50 is shown in FIG. 6 while a typical joined material test specimen 52 is shown in FIG. 7. Also shown in FIG. 7, as an example, are representative shims 56 joined together with a diffusion bond 58. In practice a plurality of representative shims 56 comprising base material are bonded together and a test specimen 52 prepared. Material properties may include, but not limited to, ultimate tensile strength, yield strength, yield tensile strength, percent elongation at failure, creep rate, creep rupture, crack propagation rate, or combinations thereof. Design temperature ($T_{Design}$) is selected to take into account safety factors and unknowns in the device and its operation. For example, $T_{Design}$ will invariably be greater than or equal to $T_{Operating}$ and may be selected as $T_{Operating}$ plus, for example, 50 deg. C. If the evaluation represented by node 202 does not produce a $JMP_{Design}$ superior or equal to $BMP_{Design}$ (node 202 is false), a conventional burst test prescribed by a pressure vessel certification organization, such as the ASME, will be satisfactory to determine the MAWP (node 208).

Figure 8:
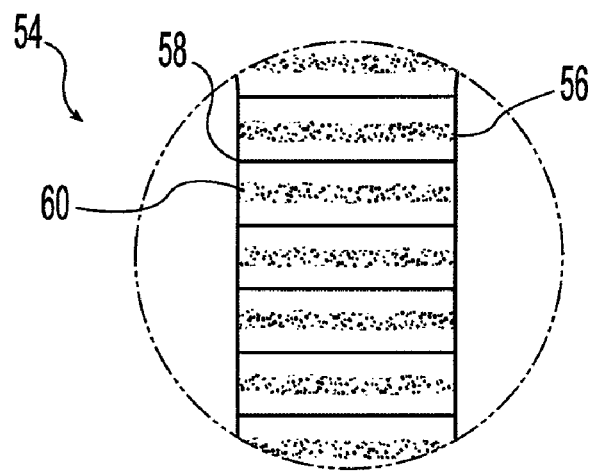
FIG. 8 is an enlarged view of a cross-section of a portion of the fabricated material test specimen indicated at 8 in FIG. 7 and illustrating grain artifacts.

If node 202 of FIG. 11 produces a true determination ($JMP_{Design}$ is superior or equal to $BMP_{Design}$) the presence or absence of spurious artifacts is determined (node 204). Such spurious artifacts are those generally unavoidable elements which may occur during manufacture and fabrication of the device. Turning to FIG. 8, they include, in a shim-based microchannel device joined with diffusion bonding, for example, metal carbide precipitates 60. Grain growth (not shown) may also exist, for example, when the grain size grows to at or near shim thickness.

Figure 9:
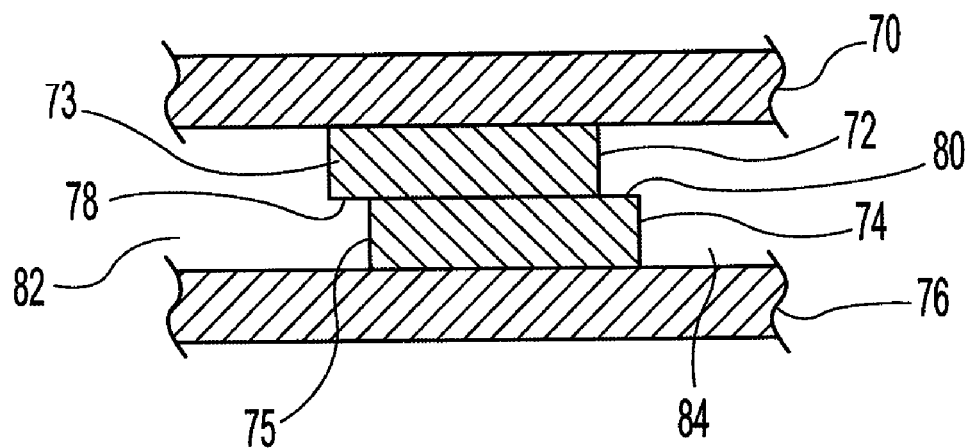
FIG. 9 is an enlarged view of a cross-section of a portion of an exemplary microchannel device and illustrating rib offset artifacts.

Turning now to FIG. 9, four representative shims 70, 72, 74, 76 are bonded together. Representative ribs 73, 75 of two of the shims 72, 74 are misaligned, producing offsets 78, 80 of the ribs 73, 75. Such offsets 78, 80, may produce additional stress concentration points as well as reduced areas of bonding and changes to the dimensions of the channels 82, 84.

Figure 10:
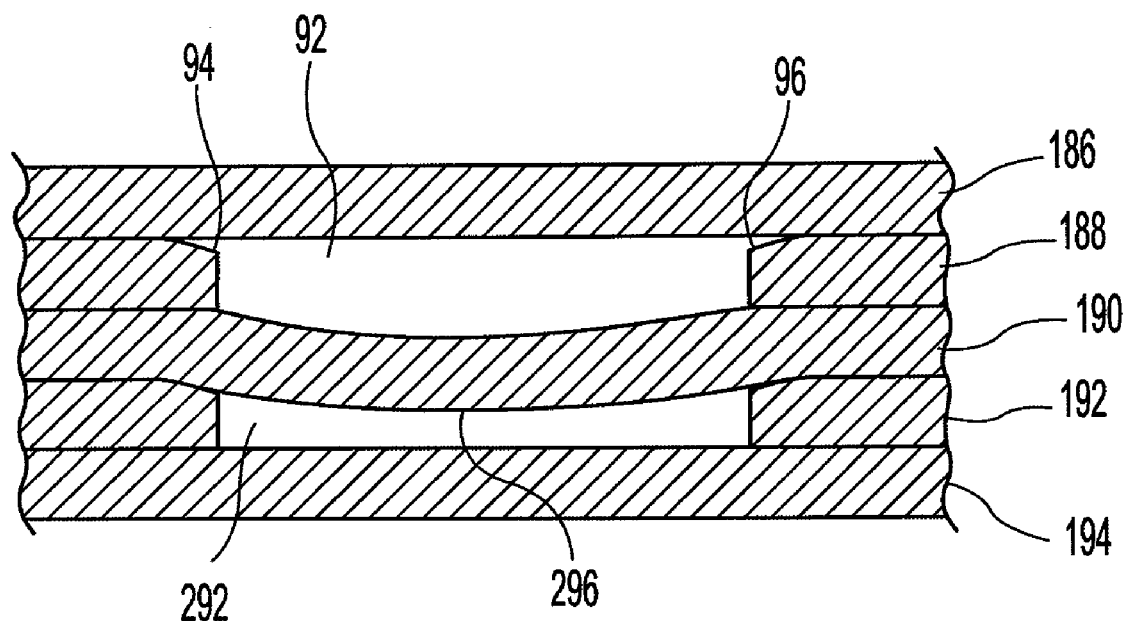
FIG. 10 is an enlarged view of a cross-section of a portion of an exemplary microchannel device and illustrating "rollover" artifacts.

Turning now to FIG. 10, in representative fashion, a top shim 186, a middle shim, 190, and a bottom shim 194 sandwich a first shim portion or rib 188 and a second shim portion 192. Formed therein are two channels 92, 292. As is illustrated in FIG. 10, notches, or rollover artifacts 94, 96 and a bowed portion 296 are present. Stamp rollover artifacts, for example, may be produced during the stamping process and may contribute to stress concentration points 94, 96. Stresses in manufacturing may also contribute to bowing artifacts 296 which can be exacerbated by rollover artifacts.

The determination of whether an artifact is, in fact, spurious, depends upon, for example, comparing the size of the stamp rollover 94, 96, the metal carbide precipitates 60, the misalignment or offset of shim ribs (FIG. 9), shim thickness (not shown), bowing of channel walls (FIG. 10), comparative channel-to-channel or layer-to-layer pressure drop, or grain size (not shown) to channel size or shim thickness.

Returning again to FIG. 11, if the evaluation represented by node 204 is true, a conventional burst test prescribed by a pressure vessel certification organization, such as the ASME, will be satisfactory to determine the MAWP (node 208). If the evaluation represented by node 204 is false, calculations promulgated by a pressure certification organization, such as the ASME, will be satisfactory to determine the MAWP (node 206).

If the determination at node 200 produces a true result ($T_{Operating}$ is greater than or equal to $T_{Threshold}$), node 210 is entered and a determination made whether a condition of an at least first material property at a low temperature for a specimen of joined material ($JMP_{Low}$) is superior or equal to the at least first material property at the low temperature for a specimen of base material ($BMP_{Low}$) is true or false. Material properties may include, but not limited to, ultimate tensile strength, yield strength, yield tensile strength, percent elongation at failure, creep rate, creep rupture, crack propagation rate, or combinations thereof. The low temperature may be selected as a less than $T_{Threshold}$ and is often selected as about room temperature or between about 20 deg. C. and about 23 deg. C.

If the determination at node 210 is false ($JMP_{Low}$ is not superior or equal to $BMP_{Low}$), at least one burst test is performed on a representative burst test device (node 214). Such tests comprise independently increasing temperature and pressure of the representative burst test device from a first state to a second state, the second state comprising a temperature greater than or equal to $T_{Threshold}$.

If the determination at node 210 is true ($JMP_{Low}$ is superior or equal to $BMP_{Low}$), node 212 is entered and a determination made whether $JMP_{Design}$ is superior or equal to $BMP_{Design}$. As will be appreciated by those skilled in the relevant art, node 212 comprises the same determination as node 202 and the description stated above will apply. If the determination at node 212 is false ($JMP_{Design}$ is not superior or equal to $BMP_{Design}$), at least one burst test is performed on a representative burst test device. Such tests comprises independently increasing temperature and pressure of the representative burst test device from a first state to a second state, the second state comprising a temperature greater than or equal to $T_{Threshold}$.

If the determination at node 212 is true ($JMP_{Design}$ is superior or equal to $BMP_{Design}$), node 216 is entered and a determination made about the presence or absence of spurious artifacts. As will be appreciated by those skilled in the relevant art, node 216 comprises the same determination as node 204 and the description stated above will apply.

If the determination at node 216 is false (no spurious artifacts), calculations promulgated by a pressure certification organization, such as the ASME, will be satisfactory to determine the MAWP (node 206).

If the determination at node 216 is true (spurious artifacts present), node 218 is entered and a determination made if the effects at $T_{Design}$ of spurious artifacts are calculable. If so, node 208 is entered and the burst test described earlier is performed. The effects of artifacts may not be calculable, for example, depending upon the size of stamp rollover, carbide precipitates, misalignment or offset of shim ribs, shim thickness, bowing of channel walls or grain size growth relative to shim thickness.

If the determination at node 218 is false ($T_{Design}$ effects of spurious artifacts not calculable), node 214 is entered and at least one burst test performed on a representative burst test device. Such tests comprise independently increasing temperature and pressure of the representative burst test device from a first state to a second state, the second state comprising a temperature greater than or equal to $T_{Threshold}$.

As noted above, a microchannel device may be extremely complex. The representative burst test device must, however, be representative of the device with respect to channel dimensions including, but not limited to, height, width, length, or combinations thereof; fabrication methods, including, but not limited to, stamping, bonding, including, but not limited to diffusion bonding, considering, but not limited to, method, time, temperature, pressure, or combinations thereof; surface preparation, including, but not limited to, finish, passivation, etching, cleaning, coating, flatness, lay, waviness, or combinations thereof; wall thicknesses; base material, including, but not limited to, alloy 617; rib dimensions; heat treat cycles; heating cycles during manufacture; shim thickness; symmetry; size scale; or combinations thereof.

Returning now to FIG. 11, node 214 comprises at least one burst test of at least one representative burst test device, the burst test comprising independently increasing the temperature and pressure of the burst test device from a first state to a second state, the second state comprising a temperature greater than or equal to the $T_{Threshold}$.

Turning now to FIGS. 12 and 16-18, a method is shown for burst testing a representative burst test device when the conditions shown in FIG. 11 apply as described above. The method comprises first heating the representative burst test device at a substantially constant rate from a first state temperature to a second state temperature, the second state temperature being greater than or equal to a $T_{Threshold}$ and allowing the device to thermally equilibrate by holding the device at substantially the second state temperature for a fixed period of time. Subsequently, the device is held at the second state temperature while being pressurized at a substantially constant rate from a first state pressure to a second state pressure and held for a fixed period of time. As shown in exemplary fashion in FIGS. 16-17 creep eventually causes the device to fail. The step of pressurizing the device may comprise introducing a pressurizing gas into the representative burst test device. Alternatively, the pressurizing gas may be preheated prior to being introduced into the device. The second state pressure may be greater than about 30 bar. The constant rate of pressurizing may be selected as being between about one bar per minute and about ten bar per minute. The constant rate of pressurizing may be below a pressure shock limit, that is, the increase in pressure does not contribute to an impact load on the material being tested. The second state temperature may be greater than about 900 deg. C. The constant rate of heating may be selected to avoid significant creep. The constant rate of heating may be selected as being between about one deg. C. per minute and about ten deg. C. per minute.

Turning now to FIGS. 13 and 19-21, a further method is shown for burst testing a representative burst test device when the conditions shown in FIG. 11 apply as described above. The method comprises first pressurizing the representative burst test device at a substantially constant rate from a first state pressure to a second state pressure and holding the device at substantially the second state pressure for a fixed period of time. Subsequently, while holding the device a substantially the second state pressure, the device is heated at a substantially constant rate from a first state temperature to failure. The second state pressure may be greater than about 30 bar. The constant rate of pressurizing may be between about one bar per minute and about ten bar per minute. The constant rate of pressurizing may be below a pressure shock limit. The constant rate of temperature increase may be selected to avoid significant creep. The constant rate of temperature increase may be between about one deg. C. per minute and about ten deg. C. per minute.

Turning now to FIGS. 14 and 22-24, a further method is shown for burst testing a representative burst test device when the conditions shown in FIG. 11 apply as described above. The method comprises first heating the representative burst test device at a substantially constant rate from a first state temperature to a second state temperature and allowing the device to thermally equilibrate. Subsequently, and while holding the device at the second state temperature, pressurizing the device at a substantially constant rate from a first state pressure to a second state pressure. The second state temperature may be selected as about $T_{Design}$ and it may be greater than about $T_{Threshold}$. The constant rate of heating may be selected to avoid significant creep. The constant rate of heating may be selected as being between about one deg. C. per minute and about ten deg. C. per minute. The second state temperature may be greater than about 900 deg. C. The constant rate of pressurizing may be selected to avoid a pressure shock limit. The constant rate of pressurizing may be selected as between about one bar per minute and about ten bar per minute. The step of pressurizing the device may further comprise pressurizing the device to failure.

This detailed description in connection with the drawings is intended principally as a description of the presently preferred embodiments of the invention, and is not intended to represent the only form in which the present invention may be configured or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

We claim:

1. A method of determining the maximum allowable working pressure (MAWP) of a microchannel device, the microchannel device comprising a plurality of shims, the shims comprising a base material and the shims joined with at least one microchannel fabrication technique, the method comprising:

(a) determining whether a condition of a device operating temperature is greater than or equal to a base material threshold temperature is true or false;

(b) determining whether a condition of an at least first material property at a low temperature for a specimen of joined material is superior or equal to the at least first material property at the low temperature for a specimen of base material is true or false when the condition of step (a) is true;

(c) conducting at least one burst test of at least one representative burst test device when the condition of step (b) is false, the burst test comprising independently increasing temperature and pressure of the at least one representative burst test device from a first state to a second state, the second state comprising a temperature greater than or equal to the base material threshold temperature;

(d) determining whether a condition of an at least first material property at a design temperature for a specimen of joined material is superior or equal to the at least first material property at the design temperature for a specimen of base material is true or false when the condition of step (b) is true;

(e) conducting at least one burst test of at least one representative burst test device when the condition of step (d) is false, the burst test comprising independently increasing temperature and pressure of the at least one burst test device from a first state to a second state, the second state comprising a temperature greater than or equal to the base material threshold temperature;

(f) determining whether a condition of the presence of at least one spurious artifact is true or false when the condition of step (d) is true;

(g) determining whether a condition of at least one effect of at least one spurious artifact on MAWP at the design temperature is calculable is true or false when the condition of step (f) is true; and (h) conducting at least one burst test of at least one representative burst test device when the condition of step (g) is false, the burst test comprising independently increasing temperature and pressure of the at least one burst test device from a first state to a second state, the second state comprising a temperature greater than or equal to the base material threshold temperature.

2. The method of claim 1, step (a) further comprising determining the device operating temperature.

3. The method of claim 2, step (a) further comprising selecting the device operating temperature from the group consisting of:
normal operating temperature;
maximum temperature caused by random operational perturbations;
maximum temperatures caused by operational changes;
maximum startup temperature; and
maximum shutdown temperature.

4. The method of claim 2, wherein the device comprises a steam methane reformer, step (a) further comprising selecting the device operating temperature from between about 800 deg. C. and about 1200 deg. C.

5. The method of claim 4, wherein the base material is a nickel alloy containing at least 35 percent nickel.

6. The method of claim 1, step (a) further comprising determining $T_{Threshold}$.

7. The method of claim 1, wherein the device is a microchannel reactor and the at least one representative burst test device is representative of the device with respect to channel dimensions including, but not limited to, height, width, length, or combinations thereof; fabrication methods, including, but not limited to, stamping, bonding, including, but not limited to diffusion bonding, considering, but not limited to, method, time, temperature, pressure, or combinations thereof; surface preparation, including, but not limited to, finish, passivation, etching, cleaning, coating, flatness, lay, waviness, or combinations thereof; wall thicknesses; base material, including, but not limited to, alloy 617; rib dimensions; heat treat cycles; heating cycles during manufacture; shim thickness; symmetry; size scale; or combinations thereof.

8. The method of claim 1, step (c), step (e), and step (h) further comprising the ordered steps of:
(A) heating the representative burst test device at a substantially constant rate from a first state temperature to a second state temperature;
(B) allowing the burst test device to thermally equilibrate;
(C) holding the representative burst test device at the second state temperature while pressurizing the representative burst test device at a substantially constant rate from a first state pressure to a second state pressure; and
(D) holding the representative burst test device at substantially the second state temperature and substantially the second state pressure for a fixed period of time.

9. The method of claim 1, step (c), step (e), and step (h) further comprising increasing the pressure at a substantially constant rate of between about one bar per minute and about ten bar per minute.

10. The method of claim 1, step (c), step (e), and step (h) further comprising the ordered steps of:
(A) pressurizing the representative burst test device at a substantially constant rate from a first state pressure to a second state pressure;
(B) holding the representative burst test device at substantially the second state pressure for a fixed period of time; and
(C) holding the representative burst test device at the second state pressure while heating the representative burst test device at a substantially constant rate from a first state temperature to failure.

11. The method of claim 1, step (c), step (e), step (h) further comprising the ordered steps of:
(A) heating the representative burst test device at a substantially constant rate from a first state temperature to a second state temperature;
(B) allowing the burst test device to thermally equilibrate; and
(C) holding the representative burst test device at the second state temperature while pressurizing the representative burst test device at a substantially constant rate from a first state pressure to an excess pressure.

12. The method of claim 1, step (c), step (e), and step (h) further comprising increasing the temperature at a substantially constant rate of between about one deg. C. per minute and about ten deg. C. per minute.

13. The method of claim 1, step (c), step (e), and step (h) further comprising pressurizing the representative burst test device to failure.

14. The method of claim 1, step (f) further comprising determining the presence of a stamp rollover, carbide precipitates, misalignment or offset of shim ribs, bowing of channel walls, grain size growth, or combinations thereof.

15. The method of claim 14, step (f) further comprising comparing the size of a stamp rollover, carbide precipitates, misalignment or offset of shim ribs, shim thickness, bowing of channel walls, or grain size growth to shim size.

16. The method of claim 14, step (f) further comprising determining the presence of grain size growth relative to shim thickness.

17. A method for burst testing a representative burst test device, the method comprising the ordered steps of:

(a) heating the device at a substantially constant rate from a first state temperature to a second state temperature, the second state temperature greater than or equal to a base material threshold temperature;
(b) allowing the device to thermally equilibrate;
(c) holding the device at the second state temperature while pressurizing the device at a substantially constant rate from a first state pressure to a second state pressure; and
(d) holding the device at substantially the second state temperature and substantially the second state pressure for a fixed period of time.

18. The method of claim 17, wherein the second state temperature is greater than about a design temperature.

19. The method of claim 18, wherein the design temperature is greater than about a threshold temperature.

20. A method for burst testing a representative burst test device, the method comprising the ordered steps of:
(a) pressurizing the representative burst test device at a substantially constant rate from a first state pressure to a second state pressure;
(b) holding the representative burst test device at substantially the second state pressure for a fixed period of time; and
(c) holding the representative burst test device at substantially the second state pressure while heating the representative burst test device at a substantially constant rate from a first state temperature to failure.

21. A method for burst testing a representative burst test device, the method comprising the ordered steps of:
(a) heating the representative burst test device at a substantially constant rate from a first state temperature to a second state temperature;
(b) allowing the burst test device to thermally equilibrate; and
(c) holding the representative burst test device at the second state temperature while pressurizing the representative burst test device at a substantially constant rate from a first state pressure to an excess pressure.

22. The method of claim 21, wherein the second state temperature is about a design temperature.

23. The method of claim 22, wherein the design temperature is greater than about a threshold temperature.

24. The method of claim 21, wherein the constant rate of heating is between about one deg. C. per minute and about ten deg. C. per minute.

25. A method of determining the maximum allowable working pressure (MAWP) of a microchannel device operating at a temperature greater to or equal to a base material threshold temperature ($T_{Threshold}$), the microchannel device comprising a plurality of shims, the shims comprising a base material and the shims joined with at least one microchannel fabrication technique, the method comprising:
(a) determining whether a condition of an at least first material property at a low temperature for a specimen of joined material superior or equal to the at least first material property at the low temperature for a specimen of base material is true or false;
(b) conducting at least one burst test of at least one representative burst test device when the condition of step (a) is false, the burst test comprising independently increasing temperature and pressure of the at least one representative burst test device from a first state to a second state, the second state comprising a temperature greater than or equal to the base material threshold temperature;
(c) determining whether a condition of an at least first material property at a design temperature for a specimen of joined material is superior or equal to the at least first material property at the design temperature for a specimen of base material is true or false when the condition of step (a) is true;
(d) conducting at least one burst test of at least one representative burst test device when the condition of step (c) is false, the burst test comprising independently increasing temperature and pressure of the at least one burst test device from a first state to a second state, the second state comprising a temperature greater than or equal to the base material threshold temperature;
(e) determining whether a condition of the presence of at least one spurious artifact is true or false when the condition of step (c) is true;
(f) determining whether a condition of at least one effect of at least one spurious artifact on MAWP at the design temperature is calculable is true or false when the condition of step (e) is true; and
(g) conducting at least one burst test of at least one representative burst test device when the condition of step (f) is false, the burst test comprising independently increasing temperature and pressure of the at least one burst test device from a first state to a second state, the second state comprising a temperature greater than or equal to the base material threshold temperature.

* * * * *

UNITED STATES PATENT AND TRADEMARK OFFICE
CERTIFICATE OF CORRECTION

PATENT NO.       : 7,552,642 B2
APPLICATION NO.  : 11/855999
DATED            : June 30, 2009
INVENTOR(S)      : Neagle et al.

It is certified that error appears in the above-identified patent and that said Letters Patent is hereby corrected as shown below:

Column 1, line 49: "foregoing materials, polymers; such as thermoset resins" should be changed to --foregoing materials, polymers, such as thermoset resins--.

Column 3, lines 46-47: "Particularized burst test procedures may burst test procedures may be satisfactory." should be deleted.

Column 6, line 14: "hearted" should be changed to --heated--.

Column 7, lines 18-19: "operating at a temperature greater to or equal to a base material" should be changed to --operating at a temperature greater than or equal to a base material--.

Column 7, line 48: "condition; determining whether a fourth condition is" should be changed to --condition is true; determining whether a fourth condition is--.

Column 7, line 51: "condition; and conducting at least one burst test of at least one" should be changed to --condition is true; and conducting at least one burst test of at least one--.

Column 10, lines 14-15: "stainless steel (e.g., 304, 316) aluminum, titanium, nickel, platinum, rhodium," should be changed to --stainless steel (e.g., 304, 316), aluminum, titanium, nickel, platinum, rhodium,--.

Column 10, line 24: "cat" should be changed to --cast--.

Column 12, line 43: "a" should be deleted.

Column 12, line 61: "tests" should be changed to --test--.

Column 13, column 29: "limited to, stamping, bonding, including, but not limited to" should be changed to --limited to, stamping, bonding, including, but not limited to,--.

Column 14, line 12: "a" should be changed to --at--.

Column 15, line 66: "limited to diffusion bonding, considering, but not limited to," should be changed to --limited to, diffusion bonding, considering, but not limited to,--, and the claim read as follows:

UNITED STATES PATENT AND TRADEMARK OFFICE
CERTIFICATE OF CORRECTION

PATENT NO. : 7,552,642 B2
APPLICATION NO. : 11/855999
DATED : June 30, 2009
INVENTOR(S) : Neagle et al.

It is certified that error appears in the above-identified patent and that said Letters Patent is hereby corrected as shown below:

7. The method of claim 1, wherein the device is a microchannel reactor and the at least one representative burst test device is representative of the device with respect to channel dimensions including, but not limited to, height, width, length, or combinations thereof; fabrication methods, including, but not limited to, stamping, bonding, including, but not limited to, diffusion bonding, considering, but not limited to, method, time, temperature, pressure, or combinations thereof; surface preparation, including, but not limited to, finish, passivation, etching, cleaning, coating, flatness, lay, waviness, or combinations thereof; wall thicknesses; base material, including, but not limited to, alloy 617; rib dimensions; heat treat cycles; heating cycles during manufacture; shim thickness; symmetry; size scale; or combinations thereof.

Column 17, line 47-column 18, line 1; "operating at a temperature greater to or equal to a base material" should be changed to --operating at a temperature greater than or equal to a base material--.

Column 18, line 9: "joined material superior or equal to the at least first" should be changed to --joined material is superior or equal to the at least first--.

The claim should read as follows:

25. A method of determining the maximum allowable working pressure (MAWP) of a microchannel device operating at a temperature greater than or equal to a base material threshold temperature ($T_{Threshold}$), the microchannel device comprising a plurality of shims, the shims comprising a base material and the shims joined with at least one microchannel fabrication technique, the method comprising:
(a) determining whether a condition of an at least first material property at a low temperature for a specimen of joined material is superior or equal to the at least first material property at the low temperature for a specimen of base material is true or false;
(b) conducting at least one burst test of at least one representative burst test device when the condition of step (a) is false, the burst test comprising independently increasing temperature and pressure of the at least one representative burst test device from a first state to a second state, the second state comprising a temperature greater than or equal to the base material threshold temperature;
(c) determining whether a condition of an at least first material property at a design temperature for a specimen of joined material is superior or equal to the at least first material property at the design temperature for a specimen of base material is true or false when the condition of step (a) is true;

UNITED STATES PATENT AND TRADEMARK OFFICE
CERTIFICATE OF CORRECTION

PATENT NO. : 7,552,642 B2
APPLICATION NO. : 11/855999
DATED : June 30, 2009
INVENTOR(S) : Neagle et al.

It is certified that error appears in the above-identified patent and that said Letters Patent is hereby corrected as shown below:

(d)     conducting at least one burst test of at least one representative burst test device when the condition of step (c) is false, the burst test comprising independently increasing temperature and pressure of the at least one burst test device from a first state to a second state, the second state comprising a temperature greater than or equal to the base material threshold temperature;

(e)     determining whether a condition of the presence of at least one spurious artifact is true or false when the condition of step (c) is true;

(f)     determining whether a condition of at least one effect of at least one spurious artifact on MAWP at the design temperature is calculable is true or false when the condition of step (e) is true; and (g)     conducting at least one burst test of at least one representative burst test device when the condition of step (f) is false, the burst test comprising independently increasing temperature and pressure of the at least one burst test device from a first state to a second state, the second state comprising a temperature greater than or equal to the base material threshold temperature.

Signed and Sealed this

Twenty-ninth Day of December, 2009

David J. Kappos
*Director of the United States Patent and Trademark Office*